(12) United States Patent
Agüeros Bazo et al.

(10) Patent No.: US 10,111,835 B2
(45) Date of Patent: Oct. 30, 2018

(54) MICROPARTICLES FOR ENCAPSULATING PROBIOTICS, PRODUCTION AND USES THEREOF

(71) Applicants: CENTRO NACIONAL DE TECNOLOGÍA Y SEGURIDAD ALIMENTARIA, LABORATORIO DEL EBRO, San Adrián-Navarra (ES); UNIVERSIDAD DE NAVARRA, Pamplona-Navarra (ES)

(72) Inventors: Maite Agüeros Bazo, Pamplona-Navarra (ES); Irene Esparza Catalán, Pamplona-Navarra (ES); Carlos Gamazo De La Rasilla, Pamplona-Navarra (ES); Carolina González Ferrero, San Adriá-Navarra (ES); Carlos Javier González navarro, San Adrián-Navarra (ES); Juan Manuel Irache Garreta, Pamplona-Navarra (ES); Rebeca Peñalba Sobrón, Pamplona-Navarra (ES); Ana Romo Hualde, San Adrián-Navarra (ES); Raquel Virto Resano, San Adrián-Navarra (ES)

(73) Assignees: CENTRO NACIONAL DE TECNOLOGÍA Y SEGURIDAD ALIMENTARIA, LABORATORIO DEL EBRO, San Adrián-Navarra (ES); UNIVERSIDAD DE NAVARRA, Pamplona-Navarra (ES)

(*) Notice: Subject to any disclaimer, the term of this patent is extended or adjusted under 35 U.S.C. 154(b) by 0 days.

(21) Appl. No.: 14/412,146

(22) PCT Filed: Jul. 5, 2013

(86) PCT No.: PCT/ES2013/070477
§ 371 (c)(1),
(2) Date: Dec. 30, 2014

(87) PCT Pub. No.: WO2014/006261
PCT Pub. Date: Jan. 9, 2014

(65) Prior Publication Data
US 2015/0335577 A1 Nov. 26, 2015

(30) Foreign Application Priority Data
Jul. 5, 2012 (ES) .................................. 201231058

(51) Int. Cl.
| | | |
|---|---|---|
| A61K 9/16 | (2006.01) |
| A23K 20/26 | (2016.01) |
| A23K 40/10 | (2016.01) |
| A23K 10/18 | (2016.01) |
| A23K 20/147 | (2016.01) |
| A23K 20/163 | (2016.01) |
| A23K 20/22 | (2016.01) |
| A23L 33/135 | (2016.01) |
| A61K 35/741 | (2015.01) |
| A61K 35/747 | (2015.01) |
| A61K 35/745 | (2015.01) |
| A23K 20/111 | (2016.01) |

(52) U.S. Cl.
CPC ............ *A61K 9/1694* (2013.01); *A23K 10/18* (2016.05); *A23K 20/111* (2016.05); *A23K 20/147* (2016.05); *A23K 20/163* (2016.05); *A23K 20/22* (2016.05); *A23K 20/26* (2016.05); *A23K 40/10* (2016.05); *A23L 33/135* (2016.08); *A61K 9/1652* (2013.01); *A61K 9/1658* (2013.01); *A61K 9/1682* (2013.01); *A61K 35/741* (2013.01); *A61K 35/745* (2013.01); *A61K 35/747* (2013.01); *A23V 2002/00* (2013.01)

(58) Field of Classification Search
CPC combination set(s) only.
See application file for complete search history.

(56) References Cited

U.S. PATENT DOCUMENTS

| | | |
|---|---|---|
| 6,159,504 A | 12/2000 | Kumabe |
| 8,834,951 B2 | 9/2014 | Harel et al. |
| 9,480,276 B2 | 11/2016 | Harel et al. |
| 9,504,275 B2 | 11/2016 | Harel et al. |

(Continued)

FOREIGN PATENT DOCUMENTS

| | | |
|---|---|---|
| CN | 1607033 A | 4/2005 |
| JP | 2010512755 A | 4/2010 |

(Continued)

OTHER PUBLICATIONS

Anal, Anil Kumar, et al. "Preparation and characterization of nanoparticles formed by chitosan—caseinate interactions." Colloids and Surfaces B: Biointerfaces 64.1 (2008): 104-110.*
Ko, J. A., et al. "Preparation and characterization of chitosan microparticles intended for controlled drug delivery." International journal of pharmaceutics 249.1 (2002): 165-174.*
Bayomi, M.A., et al., Pharm Acta Helv 73(4): 187-192,1998.
Dhanasingh, S., et al., World Academy of Science, Engineering and Technology 68: 229-233, 2010.

(Continued)

*Primary Examiner* — John Pak
*Assistant Examiner* — Daniel L Branson
(74) *Attorney, Agent, or Firm* — Tristan A. Fuierer; Moore & Van Allen, PLLC

(57) ABSTRACT

The invention relates to microparticles comprising a matrix formed by casein and chitosan, and probiotic bacteria; said matrix protects said probiotic bacteria during (i) processing, (ii) storage and (iii) transit through the gastrointestinal tract, prolonging their lifetime. The present invention also relates to the method for obtaining the microparticles and to the products and compositions incorporating them.

21 Claims, 7 Drawing Sheets

(56) References Cited

U.S. PATENT DOCUMENTS

| | | | |
|---|---|---|---|
| 2005/0226905 A1 | 10/2005 | Tien et al. | |
| 2007/0020328 A1 | 1/2007 | Lin | |

FOREIGN PATENT DOCUMENTS

| | | | |
|---|---|---|---|
| WO | 2002094224 | A2 | 11/2002 |
| WO | 2005030229 | A1 | 4/2005 |
| WO | 2011094469 | A2 | 8/2011 |
| WO | 2012021783 | A2 | 2/2012 |

OTHER PUBLICATIONS

Heidebach, T., et al., International Dairy Journal 19: 77-84, 2009.
Heidebach, T., et al., Journal of Food Engineering 98: 309-316, 2010.
Nag, A., et al., International Dairy Journal 21: 247-253, 2011.
Oliveira, A.C., et al., Journal of Microencapsulation 24(7): 685-693, 2007.
International Search Report for related International Application PCT/ES2013/070477, dated Feb. 5, 2014.
International Preliminary Examination Report for related International Application PCT/ES2013/070477, dated Aug. 8, 2014.
Russian Office Action, dated Sep. 21, 2017 (& Eng. Translation).
Imam, Elhassan M., et al.; "Controlled Drug Delivery Systems Based on Thiolated Chitosan Microspheres," Drug Development and Industrial Pharmacy, 2005, pp. 557-565, vol. 31.
Burgain, J., et al.; "Encapsulation of probiotic living cells: From laboratory scale to industrial applications," Journal of Food Engineering, 2011, pp. 467-483, vol. 104.
English Translation of Japanese Office Action, dated Jan. 23, 2018.
Kashiwagi, Hideki, et al.; "A Chitosan-Coated Tablet Was Shown to Disintegrate in Colon," Journal of Intestinal Microbiology, 2008, pp. 263-268, vol. 22.

\* cited by examiner

MICROPARTICLES FOR ENCAPSULATING PROBIOTICS, PRODUCTION AND USES THEREOF

CROSS-REFERENCE TO RELATED APPLICATIONS

This application is filed under the provisions of 35 U.S.C. § 371 and claims the priority of International Patent Application No. PCT/ES2013/070477 filed on 5 Jul. 2013 entitled "MICROPARTICLES FOR ENCAPSULATING PROBIOTICS, PRODUCTION AND USES THEREOF" in the name of Maite AGUEROS BAZO, et al., which claims priority to Spanish Patent Application No. P201231058 filed on 5 Jul. 2012, both of which are hereby incorporated by reference herein in their entirety.

FIELD OF THE INVENTION

The present invention is comprised in the scope of food, nutraceutical, cosmeceutical and pharmaceutical technology. Particularly, it relates to microparticles comprising a matrix formed by casein and chitosan and probiotic bacteria, to a method for obtaining the microparticles and to their applications.

BACKGROUND OF THE INVENTION

Generalities

The intestinal microbiota of a healthy adult is relatively stable and contains various beneficial bacterial populations made up primarily of *lactobacillus* and *bifidobacterium* species playing an important role in host health. Beneficial colonic microbiota imbalance can contribute to the development of different disorders, such as gastrointestinal tract infections, constipation, irritable bowel syndrome, inflammatory bowel disease, allergies, heart diseases and colon cancer. The World Health Organization (WHO) has recommended the use of the therapeutic and prophylactic potential of beneficial microorganisms or probiotics to prevent these risks.

Probiotics are defined as live microorganisms which provide beneficial physiological effects to the host when administered in sufficient amounts (Pérez-Luyo, 2008). In this sense, it is attributed to them: aid in lactose digestion, intestinal infection prevention, immunomodulatory action, cancer and cardiovascular disease prevention. Additionally, the possible role of probiotics in dental caries prevention is under research.

There are four basic ways for consuming probiotics: as a concentrated culture added to a drink (e.g., fruit juice, etc.), inoculated in prebiotic fibers, as a dietary supplement in lyophilized cell dosage forms (e.g., powder, capsules, tablets, etc.) and inoculated in milk-based foods.

Probiotic bacteria have been incorporated in a wide range of foods, mainly in dairy products (yoghurt, cheese, ice creams, milk-based desserts, etc.), but also in other foods such as cereals, juices, chocolate, etc.

However, the survival rate of the probiotics in these products during processing and/or preservation is very low (De Vos et al., 2010), and for these microorganisms to produce the mentioned beneficial effects, they must remain viable and be at the suitable concentration at the time of consumption. There are several factors which are responsible for reducing probiotic culture viability, such as for example, acidity at the end of food processing/production, acidity produced over the lifetime thereof or post-acidification, inhibition by fermentation metabolites, lack of nutrients, packaging permeability, osmotic pressure, storage temperature, interaction with other microbial species, etc. Generally, the more acidic the product over its lifetime, the lower the viability of probiotic bacteria such as *Bifidobacteria* and *L. acidophilus*.

The strategies for improving probiotic viability include selecting acid resistant strains, increasing the initial concentration of probiotic microorganisms, or adding a suitable prebiotic which maintains an active metabolism throughout the life thereof, a low post-acidification level, and preventing the formation of unwanted fermentation metabolites. Taking into account that probiotic concentrates are often stored for long periods of time before use and after incorporation in food and/or nutraceutical products, it is of great importance to find a system which allows maintaining bacterial viability throughout this entire time and thus prolonging the product shelf life, if possible, without needing to use specific temperature and humidity conditions to prevent additional economic costs.

A relevant aspect to be considered when using probiotics is that for them to produce the mentioned beneficial effects for human health, they must reach the colon still viable, whereby they need to overcome the barrier of the upper gastrointestinal tract, i.e., the acidity and digestive enzymes in the stomach and the bile salts in the small intestine.

Furthermore, probiotic bacteria are exposed to various stress factors during production at industrial level such as freezing, drying, exposure to oxygen, temperatures, high concentrations of lactic acid in the culture medium, etc.

In view of the foregoing, the possibility of encapsulating live probiotics as an alternative for maintaining their viability given the described adverse environmental conditions (Borgogna et al., 2010; Ding and Shah, 2008) is gaining a great interest today. These techniques have been used for several years, although the benefits obtained through them can still be improved.

Most probiotic microencapsulation methodologies designed until now are comprised in three large groups: extrusion, emulsion and spray-drying scalable to industrial level (Heidebach et al., 2011). The extrusion method is a simple and economical method that does not harm the bacteria although it is not an easily scalable technique, which makes obtaining large amounts of product difficult. Although emulsification is the technique for encapsulating probiotic bacteria most commonly described in the literature, it is a more complex technique that requires the use of surfactants and oils so it is rather unviable economically, it can affect the organoleptic properties and texture of the product in which they are incorporated and it is not suitable for developing low fat food products. Microencapsulation by means of spray-drying ("spraying") is a simple and economical process although it gives rise to a high bacterial mortality rate as a result of the simultaneous dehydration and thermal inactivation process of the microorganisms.

Generally, the most suitable microcapsules for encapsulating probiotics should comply with the following requirements (Heidebach et al., 2011):

to be obtained by means of a simple and economical process that does not compromise bacterial viability.
to have a size and characteristics that are suitable to prevent altering the organoleptic properties of the food in which they are incorporated (particles with sizes greater than 100 µm can be noticed by the consumer).
to protect the probiotics from adverse environmental conditions (matrix, processing, storage, etc.).

to stabilize the probiotics and protect them from stress derived from the conditions of the upper gastrointestinal tract.

to release the live bacteria into the intestine.

No formulation complying with all the desired requirements, or at least the most relevant requirements, has been developed until now.

One of the materials used for encapsulating probiotic bacteria is casein, a conjugated protein making up about 80% of total milk proteins. Studies have been developed using this protein alone or in combination with other polymers, including polysaccharides, for encapsulating probiotic bacteria (Heidebach et al., 2009, Heidebach et al., 2010. Oliveira et al., 2007), good encapsulation efficiency results being obtained without compromising bacterial viability. Of the three papers mentioned, the first two are based on a rather unscalable emulsification system which gives rise to very large size microcapsules (greater than 100 µm). On the other hand, studies on the resistance to acidic pH conducted in the three identified papers clearly show that the microcapsules protect the bacteria from acidity. However, none of said papers conducts the study using pepsin to reproduce the actual gastric conditions which are more aggressive than mere acidic pH (the enzyme may degrade the protein and increase the bacterial exposure to the medium). Likewise, in those papers viability studies are conducted over time, a very significant loss of bacterial counts both in the formulations of encapsulated bacteria and in the formulations of free bacteria, being lower in the case of encapsulated bacteria, being observed at 60-120 days of storage (under different conditions).

*Lactobacillus plantarum* is one of the most commonly used lactic acid bacteria; this bacterium is considered as a GRAS (Generally Recognized as Safe) organism capable of healthy colonization of human gastrointestinal tract. Many *L. plantarum* strains are marketed today as probiotics. However, *L. plantarum* is a bacterium which is very sensitive to the conditions of the gastrointestinal medium, can be kept for a very short time in storage, even under refrigeration, since its counts drops very significantly in just a few days (Ayub and Brinques, 2011).

Two papers have been published recently concerning the encapsulation of these bacteria for protecting them both during storage and during passage through the gastrointestinal barrier. In the first paper (Ayub and Brinques, 2011), the authors use different types of formulations, all of them based on alginate and/or pectin and/or chitosan, for encapsulating such bacteria. However, they fail to improve the gastrointestinal resistance and even though they improve the number of viable cells during storage at 4° C., there is still a significant reduction in the number of viable cells after 38 days of study. In another paper (Gbassi et al., 2009), the resistance of the bacteria is significantly increased after immobilizing them in an alginate matrix coated with whey proteins. However, it does not relates to microparticles but rather macroscopic particles, the organoleptic properties of which might be rather undesirable and which furthermore require lyophilization for preservation.

Another most commonly used lactic acid bacteria is *Lactobacillus casei*, the health promoting potential of which has been widely reported. It can be found in various products distributed worldwide including the traditional fermented milks such as yakult, kephir, actimel, gefilus and vifit, and in cheeses such as parmesan and manchego among others. Nevertheless, this bacterium has the same limitations as the preceding one (*L. plantarum*), i.e., it is sensitive to the conditions of the upper gastrointestinal tract and its stability during the storage periods is very limited.

Additionally, systems for encapsulating probiotic bacteria based on using alginate as an encapsulating polymer have been described and in many of those cases very large size capsules are obtained (between 700 µm and 2 mm), or rather unscalable emulsification methods are used. Although the resistance of the bacteria to acidic pH is increased in some cases when they are encapsulated, most of those papers do not conduct the studies in the presence of enzymes, so the gastrointestinal conditions are not faithfully reproduced, only the resistance to acidity being contemplated. On the other hand, these encapsulation systems also reduce the decrease in bacterial counts during storage under different conditions, however despite of that, there are still significant decreases over short time periods.

Therefore, there is still a need to develop systems which allow protecting the probiotic bacteria during processing, storage and/or transit through the gastrointestinal tract; advantageously said systems are microparticles containing the probiotic bacteria, which have a uniform size and do not interfere with the organoleptic properties of the product in which they are eventually incorporated, and are capable of protecting the probiotic bacteria during processing and storage under controlled or environmental conditions, and during transit through the gastrointestinal tract.

SUMMARY OF THE INVENTION

The inventors of the present invention have discovered microparticles solving the aforementioned problems, i.e., microparticles having the capacity of encapsulating probiotic bacteria for incorporation into foods and nutraceutical, cosmeceutical and pharmaceutical products. These microparticles protect the probiotic bacteria from being inactivated by external agents, both when processing the food or nutraceutical, cosmeceutical or pharmaceutical product in which they are incorporated, and during storage over prolonged periods under environmental or controlled condition, increasing the shelf life of these foods or nutraceutical products. Furthermore, after being taken in, they facilitate probiotic bacteria release in the desired location, protecting them from the "acidic-peptic" conditions of the upper gastrointestinal tract, particularly of the stomach.

These microparticles are stable and inert in the food or in the nutraceutical, cosmeceutical or pharmaceutical formulation in which they are incorporated, preventing the food, nutraceutical, cosmeceutical or pharmaceutical matrix from compromising the bacterial viability.

Furthermore, the inventors have developed a method for obtaining these microparticles in a simple manner which is applicable at industrial scale. This method does not include the use of surfactants or emulsifiers, synthetic polymers, or any reagent which is not approved as food additive. Furthermore, this method allows controlling the size of the obtained microparticles to be less than 100 µm to prevent them from being noticed by the consumer or from negatively affecting the organoleptic properties of the product in which they are incorporated.

The microparticles can be resuspended, but not dissolved, easily in an aqueous medium, protecting the probiotic bacterium which they contain from the medium. The microparticles of the invention remain stable in the product in which they are incorporated, so a significant decrease in the viable bacteria count after long storage periods under environmental and/or controlled conditions is prevented. Furthermore, these microparticles are applicable to different types of foods, from drinks and dairy products to solid foods, and in nutraceutical products. Likewise, said microparticles can be formulated into cosmeceutical and pharmaceutical formulations.

Additionally, it has been observed that said microparticles have a strong immunomodulatory effect and favor the induction of a T-helper 1 (Th1) response and/or shift the immune response towards Th1, therefore they can be used in the manufacture of an immune system modulating (immunomodulatory) composition for the prevention and/or treatment of an immune system impairment, for example, in the prevention and/or treatment of Th2-mediated transplant rejection, allergies and allergy-associated diseases, immunodeficiencies and pathologies derived from said immunodeficiencies, infections caused by intracellular pathogens and/or mucosal infections.

The microparticles of the invention provide a new system for encapsulating and stabilizing probiotic microorganisms. According to the present invention, casein is used in combination with chitosan as a vehicle for protecting the probiotic bacteria from the environmental conditions during long storage periods and from the gastric conditions, thus increasing their lifetime and facilitating release into the intestine, thus improving their probiotic effect. Furthermore, the casein per se has significant nutritional properties complementing the beneficial effects of the encapsulated probiotic bacterium itself.

In summary, the microparticles of the invention have the capacity to protect the probiotic bacteria during (i) processing, (ii) storage and (iii) transit through the gastrointestinal tract.

Therefore in an aspect, the invention relates to microparticles comprising a matrix and a probiotic bacterium, wherein said matrix consists in casein and chitosan.

In another aspect, the invention relates to a method for obtaining the microparticles provided by this invention, which comprises mixing a casein or a casein source, probiotic bacteria and chitosan.

In another aspect, the invention relates to a composition comprising a plurality of microparticles provided by this invention, or comprising at least one microparticle provided by this invention and a food, nutraceutical, cosmeceutical or pharmaceutical acceptable vehicle.

In another aspect, the invention relates to a food, nutraceutical, cosmeceutical or pharmaceutical product comprising the microparticles provided by this invention.

In another aspect, the invention relates to the use of said microparticle, composition or product provided by this invention in the manufacture of an immune system modulating composition, or in other words, the invention relates to said microparticle, composition or product provided by this invention for use in an immune system modulating composition. Said immunomodulatory composition favors the induction of a Th1 response and/or shifts the immune response towards Th1, preferably from Th2 towards Th1, and can be used for the prevention and/or treatment of immune system impairments, for example, in the prevention and/or treatment of (i) Th2-mediated transplant rejection, (ii) allergies and allergy-associated diseases, (iii) immunodeficiencies and pathologies derived from said immunodeficiencies, (iv) infections caused by intracellular pathogens and/or mucosal infections.

The invention also relates to a microparticle, composition or product provided by this invention for being used orally in the prevention and/or treatment of an immune system impairment, and to a microparticle, composition or product provided by this invention for being used orally in the prevention and/or the treatment of Th2-mediated transplant rejection; allergies and allergy-associated diseases; immunodeficiencies and pathologies derived from said immunodeficiencies; infections caused by intracellular pathogens, or mucosal infections.

Other more detailed aspects of the present invention will be clarified in the following sections in which specific examples showing the most relevant results, both through more thorough illustrations and explanation, are included.

DETAILED DESCRIPTION OF THE INVENTION

Figure 1:
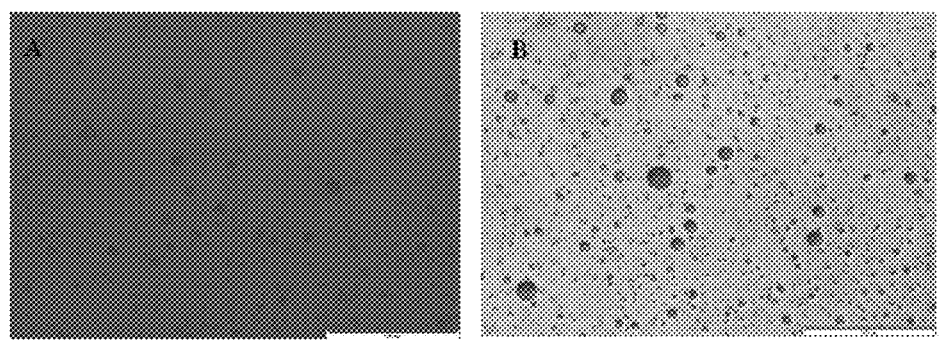
FIG. 1 shows the light microscopy images of casein microparticles modified with chitosan obtained by means of spray-drying: A) empty microparticles (×20); B) with encapsulated $L.$ $plantarum$ (×20). The horizontal line in the lower right part represents 100 μm.

The present invention relates to the production of microparticles for encapsulating probiotic bacteria, for the purpose of preventing their inactivation after incorporation into food, nutraceutical, pharmaceutical or cosmeceutical matrices or protecting them during processing and storage over prolonged storage periods under controlled or environmental conditions and, further protecting them from the "acidic-peptic" conditions during transit through the gastrointestinal tract once taken in.

Microparticles of the Invention

Therefore in one aspect, the invention relates to microparticles, hereinafter "microparticles of the invention", comprising a matrix and a probiotic bacterium, wherein said matrix consists in casein and chitosan.

As used herein, the term "microparticles" is used to designate colloidal systems of sphere types or similar shapes having a size less than 1 millimeter (mm), generally in the order of 0.5 to 999 micrometers (μm), typically in the order of 1 to 900 μm. In a particular embodiment, the microparticles of the invention have a size less than 1 mm, generally comprised between 0.1 and 999 μm, typically between 0.2 and 900 μm, advantageously between 0.3 and 500 μm, preferably between 0.4 and 250 μm, more preferably between 0.5 and 125 μm, even more preferably between 0.7 and 50 μm, still more preferably between 1 and 40 μm, even still more preferably between 2 and 12 μm approximately.

In the scope of the present invention, the term "matrix" refers to coating agent/agents or composition. According to the present invention, said matrix consists in casein and chitosan and coats the probiotic bacteria completely or partially.

The term "probiotic" is defined as a live microorganism which exerts a beneficial physiological action on host health when administered in suitable amounts (FAO/WHO 2002. Guidelines for the evaluation of probiotics in food, London).

The probiotics used in the present invention are "probiotic bacteria", i.e., live bacteria which exert a beneficial physiological action on host health when administered in suitable amounts. In a particular embodiment, said probiotic bacterium is a bacterium of the genus *Bifidobacterium* or *Lactobacillus*. In a more particular embodiment, said probiotic bacterium is selected from *L. plantarum* and *L. casei*. In a specific embodiment, the probiotic bacteria are *L. plantarum* CECT 220 and *L. casei* CECT 475 T isolated from corn silage and cheese, respectively. In another particular embodiment, said probiotic bacterium is a strain of *Bifidobacterium animalis* subsp. *lactis*, such as that marketed under the trademark BB-12®.

As used herein, the term "casein" refers to a conjugated protein making up about 80% of total milk proteins. It is a phosphoprotein type protein that falls into the definition of globulins, it is soluble; has a high water retention capacity and precipitates at a pH of about 4.6 at 20° C. It is formed by four essential fractions ($\alpha$s1-casein, $\alpha$s2-casein, $\beta$-casein and $\kappa$-casein) that are different from one another due to their amino acid composition, their charge distribution and their tendency to form aggregates in the presence of calcium. In milk, caseins form stable colloidal micelles of between 50 and 600 nm in diameter (about 150 nm on average). "Chitosan" is a natural polymer derived from the N-deacetylation of chitin (poly-N-acetyl-D-glucosamine). The deacetylation process involves the removal of acetyl groups from the molecular chain of chitin, leaving behind a complete amino group ($-NH_2$). The degree of deacetylation in a chitosan sample therefore refers to the content of free amino groups in the subunits of the polysaccharide and can be determined, for example, according to the method described by Hidalgo et al. or the ASTM F2260-03(2008) standard (Standard Test Method for Determining Degree of Deacetylation in Chitosan Salts by Proton Nuclear Magnetic Resonance Spectroscopy) among others. Generally, the degree of deacetylation of commercial chitosan is equal to or greater than 40%, preferably equal to or greater than 60%. In a particular embodiment, the degree of deacetylation of chitosan is comprised between 60% and 100%, typically between 75% and 95%, or more. Chitosan has an aminopolysaccharide structure based on the repetition of monomer units of formula (I):

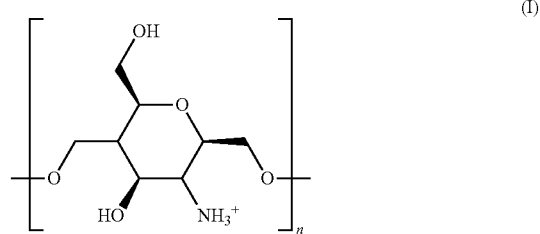

where "n" is an integer, and furthermore, an "m" number of units where the amino group is acetylated. The sum of "n+m" represents the degree of polymerization, i.e., the number of monomer units in the chitosan chain.

Chitosan is mainly protonated at acidic pH, therefore it is a positively charged polysaccharide at acidic pH.

The molecular weight of chitosan can vary within a wide range; nevertheless, in a particular embodiment, the molecular weight of the chitosan used for obtaining the microparticles of the invention is comprised between 5 and 850 kDa, typically between 25 and 300, preferably between 40 and 200 kDa, more preferably between 50 and 150 kDa.

In the scope of the present invention it is understood that as an alternative to chitosan a derivative thereof can be used, such derivative being understood as a chitosan in which one or more hydroxyl groups and/or one or more amino groups have been modified. These derivatives include, among others, acetylated, alkylated or sulfonated chitosans, as well as thiolated derivatives, as described by Roberts, Chitin Chemistry, Macmillan, 1992, 166. When a derivative is used, it is preferably selected from O-alkyl ethers of chitosan, O-acyl esters of chitosan, trimethylchitosan, chitosans modified with polyethylene glycol, etc. Other possible derivatives include salts, such as chitosan citrate, chitosan nitrate, chitosan lactate, chitosan phosphate, chitosan glutamate, etc. In any case, the person skilled in the art can identify the modifications that can be made on the chitosan without affecting the commercial stability and viability of the end formulation. In a particular embodiment, the chitosan derivative is a hydrophilically modified chitosan; as used herein, a "hydrophilically modified chitosan" is a chitosan modified with a hydrophilic group, such as a group which increases chitosan solubility in an aqueous medium, for example, an alkylated chitosan (e.g., trimethylchitosan, etc.), a sulfonated chitosan, a thiolated chitosan, a chitosan salt (e.g., glutamate, chloride, lactate, acetate, etc.), a quito-oligosaccharide, etc. In another particular embodiment, the chitosan derivative is not a hydrophobically modified chitosan; as used herein, a "hydrophobically modified chitosan" is a chitosan modified with a hydrophobic group, i.e., with a group which reduces chitosan solubility in an aqueous medium, for example, an alkyl or aryl group with a sufficient size so as to confer increased hydrophobicity to chitosan, for example, fatty acids or aldehyde residues, preferably saturated or unsaturated fatty acids of 3 to 18 carbon atoms, such as for example, palmitic acid, lauric acid, oleic acid, linoleic acid, linolenic acid, caproic acid, caprylic acid, stearic acid, propanoic acid or butyric acid. In another particular embodiment, when the matrix of the microparticle of the invention consists in casein and a chitosan derivative, such as a hydrophobically modified chitosan, the microparticle of the invention lacks an external coating consisting of alginate or hydrophobically modified alginate (alginate modified with a hydrophobic group, as defined previously with respect to the hydrophobically modified chitosan).

As mentioned above, the chitosan and casein make up the matrix which is part of the microparticles of the invention. The chitosan:casein by weight ratio can vary within a wide range; nevertheless, in a particular embodiment, said chitosan:casein by weight ratio is 1:1-150, preferably 1:5-100, more preferably about 1:14-40.

The amount of probiotic bacteria per unit of weight of the matrix that may present in the microparticles of the invention can vary within a wide range; nevertheless, in a particular embodiment, the microparticles of the invention comprise at least $10^6$ colony forming units per milligram (CFU/mg) of matrix, generally between $10^6$ CFU/mg and $5 \times 10^{13}$ CFU/mg, preferably between $10^8$ CFU/mg and $10^{12}$ CFU/mg.

In a particular embodiment, the microparticles of the invention further comprise a cross-linking agent. Non-limiting, illustrative examples of said cross-linking agents include divalent metal cations which are pharmaceutically or cosmetically acceptable, or are suitable for use in human or animal food; tripolyphosphates; and generally any substance capable of establishing a chemical interaction with casein and/or chitosan.

As used herein, a "divalent metal cation which is pharmaceutically or cosmetically acceptable, or is suitable for use in human or animal food", is a cation originating from any metal element the valence of which is 2, such as a alkaline earth metal, for example, calcium, magnesium, zinc, etc., or, if it has several valences, one of them is 2, for example, iron, etc., with the proviso that it is pharmaceutically or cosmetically acceptable, or is suitable for use in food; in a particular embodiment, said divalent metal cation is selected from the group consisting of $Ca^{2+}$, $Mg^{2+}$, $Zn^{2+}$, $Fe^{2+}$ and combinations thereof. As will be understood by the person skilled in the art, the divalent metal cation useful as cross-linking agent can be provided by a suitable source of said metal cation, such as a compound which gives rise to said divalent metal cation in an aqueous solution, for example, calcium chloride, calcium acetate, calcium gluconate, calcium lactate, calcium sorbate, calcium ascorbate, calcium citrate, calcium propionate, calcium sulfate, etc., or mixtures of said compounds.

As used herein, a "tripolyphosphate" is a compound comprising polyphosphate penta-anion which is the conjugated base of triphosphoric acid, for example, sodium tripolyphosphate, commonly identified as STPP (sodium tripolyphosphate) or simply as "TPP".

Additional examples of substances capable of establishing a chemical interaction with casein and/or chitosan, which can be used as cross-linking agents in the present invention include vanillin [3-methoxy-4-hydroxybenzaldehyde], genipin [methyl (1R,2R,6S)-2-hydroxy-9-(hydroxymethyl)-3-oxabicyclo[4.3.0]nona-4,8-diene-5-carboxylate], etc.

In a particular embodiment, the cross-linking agent is a divalent metal cation selected from the group consisting of $Ca^{2+}$, $Mg^{2+}$, $Zn^{2+}$, $Fe^{2+}$ and combinations thereof, a tripolyphosphate; vanillin; genipin; or any combination thereof. In a more particular embodiment, the cross-linking agent is the calcium cation ($Ca^{2+}$), TPP or vanillin. In another particular embodiment, the cross-linking agent is $Ca^{2+}$ and the cross-linking further comprises subjecting the mixture containing the matrix consisting in casein and chitosan, the probiotic bacteria and the cross-linking agent to a pressure treatment, such as to a hydrostatic pressure cycle, at a pressure comprised between 100 and 800 MPa.

In a particular embodiment, the microparticles of the invention comprise two or more cross-linking agents, preferably two different cross-linking agents; illustrative examples of said combinations of two different cross-linking agents eventually present in the microparticles of the invention include the binary combinations of:

a tripolyphosphate, for example, TPP, and vanillin;
a tripolyphosphate, for example, TPP, and genipin;
a tripolyphosphate, for example, TPP, and a divalent metal cation which is pharmaceutically or cosmetically acceptable, or is suitable for use in human or animal food, such as for example, a divalent metal cation selected from the group consisting of $Ca^{2+}$, $Mg^{2+}$, $Zn^{2+}$, $Fe^{2+}$ and combinations thereof;
vanillin and genipin;
vanillin and a divalent metal cation which is pharmaceutically or cosmetically acceptable, or is suitable for use in human or animal food, such as for example, a divalent metal cation selected from the group consisting of $Ca^{2+}$, $Mg^{2+}$, $Zn^{2+}$, $Fe^{2+}$ and combinations thereof;
genipin and a divalent metal cation which is pharmaceutically or cosmetically acceptable, or is suitable for use in human or animal food, such as for example, a divalent metal cation selected from the group consisting of $Ca^{2+}$, $Mg^{2+}$, $Zn^{2+}$, $Fe^{2+}$ and combinations thereof.

If the microparticles of the invention include at least one cross-linking agent, the by weight ratio of the cross-linking agent and the matrix consisting in casein and chitosan can vary within a wide range, depending on the type of cross-linking agent. In a particular embodiment, when the cross-linking agent is TPP, the cross-linking agent (TPP):matrix (casein and chitosan) ratio is 1:0.1-800, advantageously 1:1-500, preferably about 1:100-300 approximately. In another particular embodiment, when the cross-linking agent is vanillin, the cross-linking agent (vanillin):matrix (casein and chitosan) ratio is 1:0.1-500, advantageously 1:1-250, preferably about 1:50-100 approximately. In another particular embodiment, when the cross-linking agent is $Ca^{2+}$, the cross-linking agent ($Ca^{2+}$ or $Ca^{2+}$ source):matrix (casein and chitosan) ratio is 1:0.1-50, advantageously 1:1-25, preferably about 1:6-16 approximately.

In another particular and optional embodiment, the microparticles of the invention further comprise a compound protecting the matrix and the probiotic bacteria during the process of drying the microparticles, or of drying the suspension containing the microparticles of the invention by means of conventional methods, for example, by means of spray drying, hereinafter, "protective agent". Virtually, any compound complying with those characteristics can be used as a protective agent. In a particular embodiment, said protective agent is a saccharide or generally a suitable food additive which, in addition to the protective role, acts as a prebiotic. As used herein, the term "prebiotic" refers to a non-digestible food ingredient which stimulates probiotic growth and/or activity. Non-limiting, illustrative examples of protective agents which can be used within the context of the present invention include lactose, mannitol, sucrose, maltodextrin, glucose, sorbitol, etc., as well as substances with prebiotic characteristics, such as for example, oligofructose, pectin, inulin, galacto-oligosaccharides, lactulose, human milk oligosaccharides, dietary fiber, etc., and any combination thereof. In a particular embodiment, the protective agent is mannitol or sucrose. If the microparticles of the invention include a protective agent, the by weight ratio of the matrix consisting in casein and chitosan and the protective agent can vary within a wide range; nevertheless, in a particular embodiment, the matrix (casein and chitosan):protective agent by weight ratio is 1:0.1-5, typically 1:0.5-4, preferably about 1:1.

Method for Obtaining the Microparticles of the Invention

In another aspect, the invention relates to a method, hereinafter "method of the invention", for obtaining microparticles comprising a matrix and a probiotic bacterium, wherein said matrix consists in casein and chitosan (microparticles of the invention), which comprises mixing casein or a casein source, probiotic bacteria and chitosan.

The casein can be incorporated as such or can be provided by a casein source. For the sake of simplicity, the terms "casein" and "casein source" are used interchangeably in this description. Virtually any casein source can be used to put the method of the invention into practice. The casein source may have a very different origin, for example, milk, beans, etc. In a particular embodiment, the casein source is in the form of an aqueous solution or suspension; in this case, the casein can be in the form of caseinic acid or caseinate, for example, sodium caseinate, etc., or any other soluble form of casein. Even though other caseinates, for example, calcium or phosphocalcium caseinate can be used, in practice it is more advantageous to use sodium caseinate.

The aqueous solution or suspension containing the casein source can be obtained by conventional methods known by the persons skilled in the art, for example, by means of adding the casein source to an aqueous medium. As used herein, an "aqueous medium" is a medium comprising water, preferably a medium containing mainly water, more preferably the aqueous medium consists essentially of water. The amount of casein that can be contained in said aqueous solution can vary within a wide range; nevertheless, in a particular embodiment, the amount of casein contained in said aqueous solution is comprised between 0.1% and 10% (w/v), preferably between 0.5% and 5%, more preferably between 1% and 2%. Said aqueous solution of casein preferably does not contain any organic solvent.

To put the method of the invention into practice, a suspension of probiotic bacteria is advantageously prepared. Although virtually any probiotic bacterium can be used, in a particular embodiment, said probiotic bacterium is a bacterium of the genus *Bifidobacterium* or *Lactobacillus*. In a more particular embodiment, said probiotic bacterium is *L. plantarum* or *L. casei*. In a specific embodiment, the probiotic bacteria are *L. plantarum* CECT 220 and *L. casei* CECT 475 T. In another particular embodiment, said probiotic bacterium is a strain of *Bifidobacterium animalis* subsp. *lactis*, such as that marketed under the trademark BB-12®. The bacterial suspension comprises, in addition to the probiotic bacteria, a medium suitable for the corresponding probiotic bacteria. Said media are known by the persons skilled in the art. In a particular embodiment, when said probiotics are bacteria of the genus *Lactobacillus*, for example, *L. plantarum* or *L. casei*, said medium comprises broth for *Lactobacillus* according to De Man, Rogosa and Sharpe, such as that identified as 110661 MRS broth (Merck) [MRS broth]; said medium allows lactobacilli and other lactic acid bacteria to grow well and is commonly used for culturing and enriching lactobacilli from clinical samples and foods, particularly dairy products. Generally, the MRS medium comprises (in g/L): 10 g polypeptone; 10 g meat extract, 5 g yeast extract, 20 g glucose, 1.08 ml Tween® 80 (polyethoxylated sorbitan monooleate or polysorbate 80), 2 g potassium phosphate, 5 g sodium acetate, 2 g ammonium citrate, 0.2 g magnesium sulfate, 0.05 g manganese sulfate. The pH of the medium at a temperature of 25° C. is 6.4±0.2. This culture medium allows abundant development of all *lactobacillus* species. Peptone and glucose are the source of nitrogen, carbon and other elements necessary for bacterial growth. The polyethoxylated sorbitan monooleate, magnesium, manganese and acetate provide co-factors and can inhibit the development of some microorganisms. Ammonium citrate acts as an inhibitory agent inhibiting the growth of Gram negative bacteria.

The amount of probiotic bacteria which may present in the bacterial suspension can vary within a wide range; nevertheless, in a particular embodiment, the amount of probiotic bacteria present in the bacterial suspension is at least $10^6$ CFU/ml, generally between $10^6$ and $5\times10^{12}$ CFU/ml, preferably between $10^8$ and $10^{12}$ CFU/ml. In a particular and optional embodiment, the bacterial suspension also contains a saccharide, such as sucrose or other suitable disaccharide, such as for example, maltose or trehalose; these compounds generally play an important role during the process of drying the microparticles since they protect both cell membrane and proteins. The disaccharides form hydrogen bonds with the proteins when dehydration occurs, which allows maintaining the protein structure and preventing denaturation. On the other hand, it seems that sugars may be able to act as water molecule substitutes during dehydration, surrounding the polar groups both of the phospholipid bilayers and of the membranes, maintaining the structural integrity of the membrane and of the proteins. If said bacterial suspension contains a disaccharide for the indicated purposes, for example, a sucrose, the amount of disaccharide (e.g., sucrose) present in said bacterial suspension will be comprised between 0.1% and 10% (w/v) of disaccharide (e.g., sucrose), preferably between 1% and 3% (w/v). Regarding chitosan, virtually any chitosan, or suitable derivative thereof can be used to put the method of the invention into practice; nevertheless, in a particular embodiment, said chitosan has a degree of deacetylation comprised between 60 and 100%, preferably between 75% and 95%, and a molecular weight comprised between 5 and 850 kDa, typically between 25 and 300 kDa, preferably between 40 and 200 kDa, more preferably between 50 and 150 kDa. In a particular embodiment, the chitosan is in the form of an aqueous solution or suspension. The aqueous solution or suspension containing chitosan can be obtained by conventional methods known by the persons skilled in the art, for example, by means of adding chitosan to an aqueous medium, for example, water or a medium containing mainly water. The amount of chitosan which can be contained in said aqueous solution or suspension can vary within a wide range; nevertheless, in a particular embodiment, the amount of chitosan contained in said aqueous solution or suspension is comprised between 0.05% and 1% (w/v), preferably between 0.1% and 0.3%, more preferably between 1% and 2%. Said aqueous solution or suspension of chitosan preferably does not contain any organic solvent.

The order in which the casein, the probiotic bacteria and the chitosan are mixed in the mixing step of the method of the invention is irrelevant. In a particular embodiment, the casein and the probiotic bacteria are mixed first, and then the chitosan is added; in another particular embodiment, the casein and the chitosan are mixed first, and then the probiotic bacteria are added; in another particular embodiment, the probiotic bacteria and the chitosan are mixed first, and then the casein is added; and in another particular embodiment, the casein, the probiotic bacteria and the chitosan are added and mixed. In a particular embodiment, as mentioned above said components are added in the form of an aqueous solution of casein, a suspension of probiotic bacteria and an aqueous solution of chitosan.

The casein, probiotic bacteria and chitosan are preferably mixed at room temperature, i.e., at a temperature comprised between 18° C. and 25° C., preferably between 20° C. and 22° C., so as to not affect the viability of the probiotic bacteria, advantageously under stirring.

The by weight ratio of the casein and the chitosan present in the mixture prior to the formation of the microparticles of the invention can vary within a wide range; nevertheless, in a particular embodiment, said casein:chitosan by weight ratio is 1:0.01-0.5, preferably 1:0.01-0.1, more preferably about 1:0.02-0.07, or in other words, the by weight ratio of chitosan:casein present in the mixture prior to the formation of the microparticles of the invention is 1:1-150, preferably 1:5-100, more preferably about 1:14-40.

The ratio of the probiotic bacteria and the matrix components (casein and chitosan) present in the mixture prior to the formation of the microparticles of the invention can vary within a wide range; nevertheless, in a particular embodiment, said probiotic bacteria/matrix ratio is at least $10^6$ CFU per mg of matrix, generally comprised between $10^6$ CFU/mg and $10^{13}$ CFU/mg, preferably between $10^9$ CFU/mg and $10^{12}$ CFU/mg.

As mentioned above in a particular embodiment, the microparticles of the invention further comprise a cross-linking agent, such as for example, a tripolyphosphate (e.g., sodium tripolyphosphate (TPP)); vanillin; genipin; a divalent metal cation which is pharmaceutically or cosmetically acceptable, or is suitable for use in human or animal food, such as for example, a divalent metal selected from the group consisting of $Ca^{2+}$, $Mg^{2+}$, $Zn^{2+}$, $Fe^{2+}$ and combinations thereof; or any combination thereof, or any other substance capable of establishing a chemical interaction with the casein and/or the chitosan. In another particular embodiment, the microparticles of the invention comprise two or more cross-linking agents, preferably the combinations of two different cross-linking agents mentioned above with respect to the microparticles of the invention.

If the microparticles of the invention comprise at least one cross-linking agent, the method of the invention comprises adding said at least one cross-linking agent to the mixture of casein, probiotic bacteria and chitosan. In a particular embodiment, the cross-linking agent (or agents) can be added to said mixture in the form of an aqueous solution. When the cross-linking agent is the calcium cation ($Ca^{2+}$), this can be provided by a suitable source of said cation, such as a compound which gives rise to said divalent cation in an aqueous solution, for example, calcium chloride, calcium acetate, calcium gluconate, calcium lactate, calcium sorbate, calcium ascorbate, calcium citrate, calcium propionate, calcium sulfate, etc., or mixtures of said compounds. If the microparticles of the invention include a cross-linking agent, the amount of cross-linking agent to be added depends on the nature of the cross-linking agent as mentioned above with respect to the microparticles of the invention. In any case, said cross-linking agent will be added in a sufficient amount so that, when the cross-linking agent is TPP, the cross-linking agent (TPP):matrix (casein and chitosan) ratio is 1:0.1-800, advantageously 1:1-500, preferably about 1:100-300 approximately; when the cross-linking agent is vanillin, the cross-linking agent (vanillin):matrix (casein and chitosan) ratio is 1:0.1-500, advantageously 1:1-250, preferably about 1:50-100 approximately; and when the cross-linking agent is $Ca^{2+}$, the cross-linking agent ($Ca^{2+}$ or calcium source):matrix (casein and chitosan) ratio is 1:0.1-50, advantageously 1:1-25, preferably about 1:6-16 approximately.

After mixing the casein, the probiotic bacteria and the chitosan under the aforementioned conditions, i.e., at room temperature and under stirring, the microparticles of the invention comprising a matrix consisting in casein and chitosan, and a probiotic bacterium are formed. In a particular embodiment, said microparticles of the invention are in suspension in the medium in which they have been formed.

Next, if desired, the suspension resulting from the mixing of casein, probiotic bacteria and chitosan which contains the microparticles of the invention is subjected to a drying treatment by conventional methods, advantageously by means of spray drying or by means of lyophilization, in order to dry the microparticles of the invention; this drying treatment allows obtaining the microparticles of the invention in the form of powder, which contributes to increasing the stability thereof. In a particular embodiment, this drying treatment, particularly when it is performed by means of spray drying or by means of lyophilization, comprises adding a protective agent as mentioned above with respect to the microparticles of the invention, that protects the matrix and the probiotic bacteria during the drying process thereof, such as for example, a saccharide or generally a suitable food additive, which in addition to the protective role, acts as a prebiotic. Non-limiting, illustrative examples of saccharides which can be used as protective agents within the context of the present invention include lactose, mannitol, sucrose, maltodextrin, glucose, sorbitol, etc., as well as polysaccharides with prebiotic characteristics, such as for example, oligofructose, pectin, inulin, galacto-oligosaccharides, lactulose, human milk oligosaccharides, dietary fiber, etc. In a particular embodiment, the protective agent is mannitol. If the microparticles of the invention include a protective agent, this is added in the suitable amount; even though the by weight ratio of the matrix consisting in casein and chitosan and the protective agent can vary within a wide range, in a particular embodiment, the matrix (casein and chitosan):protective agent by weight ratio is 1:0.1-5, typically 1:0.5-4, preferably about 1:1.

In a particular embodiment in which the method of the invention comprises drying the suspension of microparticles of the invention, said suspension and microparticles of the invention are dried by means of spray drying; to that end, the suspension containing the microparticles of the invention and/or the mixture of casein, probiotic bacteria and chitosan, and optionally a cross-linking agent and/or a protective agent, is introduced in a spray-dryer and the processing conditions [air inlet temperature, air outlet temperature, air pressure, sample pumping rate, suction, and airflow] are controlled. The person skilled in the art can set the processing conditions that are most suitable for each case.

If desired, the method of the invention can include an additional step for stabilizing the microparticles of the invention. In a particular embodiment, when the cross-linking of the microparticles of the invention is performed by means adding a cross-linking agent, for example, a divalent metal cation, such as $Ca^{2+}$, and high pressure treatment, the method of the invention comprises introducing the suspension containing the microparticles of the invention further comprising a cross-linking agent, and/or the mixture comprising casein, probiotic bacteria, chitosan and cross-linking agent, into a suitable container, for example, a plastic bag which is sealed and subjected to at least one hydrostatic pressure cycle, at a pressure comprised between 100 and 800 MPa, preferably between 100 and 400 MPa, for a time period comprised between 1 and 30 minutes, preferably between 2 and 10 minutes. In a particular embodiment, said high hydrostatic pressure treatment comprises applying on said mixture comprising casein, probiotic bacteria, chitosan and cross-linking agent a 5-minute cycle at 100 MPa, or a 2-minute cycle at 300 MPa. In a specific embodiment, the mixture comprising casein, probiotic bacteria, chitosan and cross-linking agent ($Ca^{2+}$ is subjected to a 5-minute cycle at 100 MPa. This high pressure treatment is applied on the mixture comprising casein, probiotic bacteria, chitosan and cross-linking agent before subjecting it to the process of drying by means of spray-drying. Alternatively, as the person skilled in the art knows, the high pressure treatment is a treatment which allows cross-linking the microparticles per se without the need to incorporate a cross-linking agent, so the microparticles of the invention could be cross-linked by subjecting them to a treatment with high pressures, in the absence of cross-linking agent.

The method of the invention allows obtaining the microparticles of the invention in the form of a dry powder, which contributes to the stability of the microparticles of the invention during long storage periods under controlled or environmental conditions and it can also be easily incorporated in different intended solid and liquid products (e.g., foods, etc.).

The microparticles obtainable by means of the method of the invention have the characteristics of the microparticles of the invention and constitute an additional aspect of the present invention.

Applications

The microparticles of the invention have the capacity to encapsulate probiotic bacteria and to protect them during processing (obtaining microparticles comprising a matrix consisting in casein and chitosan, loaded with said probiotic bacteria) and storage over prolonged storage periods under controlled or environmental conditions and also to protect them from the "acidic-peptic" conditions during transit through the gastrointestinal tract once taken in; the inactivation of the probiotic bacteria after incorporation in the different intended products (e.g., foods, etc.) is thus prevented or substantially reduced.

Additionally, the microparticles of the invention have a strong immunomodulatory effect, therefore they can be used in the manufacture of an immune system modulating composition for the prevention and/or treatment of immune system impairments.

Therefore in another aspect, the invention relates to a composition, hereinafter "composition of the invention", selected from:

(i) a composition consisting in a plurality of microparticles of the invention, or in a plurality of microparticles obtainable by means of the method of the invention, or in a plurality of microparticles of the invention and of microparticles obtainable by means of the method of the invention; and (ii) a composition comprising at least one microparticle of the invention, and/or a microparticle obtainable by means of the method of the invention, and a food, nutraceutical, cosmeceutical or pharmaceutical acceptable vehicle.

The characteristics of the microparticles of the invention have already been defined above and are incorporated herein by reference. In a particular embodiment, the mean size of the microparticles of the invention is comprised between 0.5 and 125 µm, preferably between 1 and 40 µm, more preferably between 2 and 12 µm. "Mean size" is understood as the average diameter of the microparticle population, moving together in an aqueous medium. The mean size of these systems can be measured by standard methods known by the person skilled in the art and are described in the experimental part below, for example. In another particular embodiment, the probiotic bacteria present in the microparticles of the invention are selected from bacteria of the genus *Bifidobacterium* and *Lactobacillus*; in a more particular embodiment, said probiotic bacterium is selected from *L. plantarum* and *L. casei*. In a specific embodiment, the probiotic bacteria are *L. plantarum* CECT 220 and *L. casei* CECT 475 T. In another particular embodiment, said probiotic bacterium is a strain of *Bifidobacterium animalis* subsp. *lactis*, such as that marketed under the trademark BB-12®.

In another particular embodiment, the microparticles of the invention comprise a cross-linking agent as mentioned above, for example, TPP, vanillin or a divalent metal cation, for example, $Ca^{2+}$. In another particular embodiment, the microparticles of the invention comprise two or more cross-linking agents, preferably the combinations of two different cross-linking agents mentioned above with respect to the microparticles of the invention. In another particular embodiment, the microparticles of the invention comprise a protective agent, such as a saccharide, for example, mannitol. In another particular embodiment, the microparticles of the invention are in the form of a dry powder.

In the first case, the composition of the invention (i) is made up only and exclusively of microparticles of the invention and/or of microparticles obtainable by means of the method of the invention. In a particular embodiment, said composition of the invention (i) is selected from:

a composition A, comprising:
casein, between 40% and 60% by weight,
chitosan, between 0.1% and 3.5% by weight,
probiotic bacteria, between $10^9$ CFU/g and $5 \times 10^{12}$ CFU/g,
sodium tripolyphosphate, between 0% and 0.15% by weight, and
protective agent, between 0% and 60% by weight;
where the proportions by weight refer to the total weight of the composition;

a composition B, comprising:
casein, between 40% and 60% by weight,
chitosan, between 0.1% and 3.5% by weight,
probiotic bacteria, between $10^9$ cfu/g and $5 \times 10^{12}$ CFU/g,
vanillin, between 0% and 0.6% by weight, and
protective agent, between 0% and 60% by weight;
where the proportions by weight refer to the total weight of the composition; and a composition C, comprising:
casein, between 40% and 60% by weight,
chitosan, between 0.1% and 3.5% by weight,
probiotic bacteria, between $10^9$ CFU/g and $5 \times 10^{12}$ CFU/g,
$Ca^{2+}$, between 0% and 10% by weight, and
protective agent, between 0% and 60% by weight,
where the proportions by weight refer to the total weight of the composition.

In the second case, the composition of the invention (ii) comprises at least one microparticle of the invention and/or a microparticle obtainable by means of the method of the invention, and a food, nutraceutical, cosmeceutical or pharmaceutical acceptable vehicle.

In a particular embodiment, the composition of the invention is a food or feed comprising at least one microparticle of the invention and/or a microparticle obtainable by means of the method of the invention, or a composition comprising a plurality of microparticles of the invention and/or of microparticles obtainable by means of the method of the invention. As used herein, the term "food" is any substance or product of any nature, solid or liquid, natural or processed which due to its characteristics, applications, components, preparation and state of preservation, can usually or ideally be used for some of the following purposes: a) as normal nutrition for human beings or animals or as pleasurable foods; or b) as dietetic products, in special cases of human or animal food. The term "feed" includes all the natural materials and finished products of any origin which, separately or conveniently mixed with one another, are suitable as animal food. A ready-to-eat food is that which does not need to be diluted by means of an aqueous solution suitable for consumption for example. In principle, the ingredients present in a ready-to-eat food are balanced and there is no need to add additional ingredients to the food to make it ready to eat, such considered by a person skilled in the art. A concentrated food is that in which one or more ingredients are present at a higher concentration than in a ready-to-eat food, therefore for use it is necessary to dilute it by means of an aqueous solution suitable for consumption for example. Non-limiting, illustrative examples of foods provided by this invention include both dairy products and derivatives, for example, fermented milks, yoghurt, kephir, curd, cheeses, butters, ice creams, milk-based desserts, etc., and non-dairy products, such as baked products, cakes and pastries, cereals, chocolates, jams, juices, other fruit derivatives, oils and margarines, prepared dishes, etc.

In another particular embodiment, the composition of the invention is a nutraceutical composition comprising at least one microparticle of the invention and/or a microparticle obtainable by means of the method of the invention, or a composition comprising a plurality of microparticles of the invention and/or of microparticles obtainable by means of the method of the invention. As used herein, the term "nutraceutical composition" refers to a composition suitable for use in human beings or animals, comprising one or more natural products with therapeutic action which provide a health benefit or have been associated with disease prevention or reduction, for example, probiotic bacteria, etc., and it includes dietary supplements presented in a non-food matrix (e.g., capsules, powder, etc.) of a concentrated natural bioactive product usually present (or not) in the foods and which, when taken in a dose higher than that existing in those foods, exerts a favorable effect on health which is greater than effect which the normal food may have. Therefore, the term "nutraceutical composition" includes isolated or purified food products as well as additives or food supplements which are generally presented in dosage forms normally used orally, for example, capsules, tablets, sachets, drinkable phials, etc.; such products provide a physiological benefit or protection against diseases, generally against chronic diseases. If desired, the nutraceutical composition provided by the invention can contain, in addition to the probiotic bacteria, one or more nutraceuticals (products or substances associated with disease prevention or reduction), for example, flavonoids, omega-3 fatty acids, etc., and/or one or more prebiotics (non-digestible food ingredients which stimulate probiotic activity and/or growth), for example, oligofructose, pectin, inulin, galacto-oligosaccharides, lactulose, human milk oligosaccharides, dietary fiber, etc.

In another particular embodiment, the composition of the invention is a pharmaceutical composition comprising at least one microparticle of the invention and/or a microparticle obtainable by means of the method of the invention, or a composition comprising a plurality of microparticles of the invention and/or of microparticles obtainable by means of the method of the invention, suitable for oral, topical, rectal or vaginal administration; to that end, said composition comprises a pharmaceutically acceptable vehicle comprising one or more excipients suitable for oral administration, for example, in the form of capsule, powder, granulate, tablet (coated or non-coated), sachet, matrix, suspension, etc., or a pharmaceutically acceptable vehicle comprising one or more excipients suitable for topical administration, for example, in the form of cream, ointment, salve, etc., or a pharmaceutically acceptable vehicle comprising one or more excipients suitable for rectal administration, for example, in the form of suppository, etc., or a pharmaceutically acceptable vehicle comprising one or more excipients suitable for vaginal administration, for example, in the form of bolus, suppository, etc. Information about excipients suitable for the formulation of pharmaceutical compositions intended for oral, topical, rectal or vaginal administration, as well as about the production of said pharmaceutical compositions can be found in the book "Tratado de Farmacia Galénica", by C. Faulí i Trillo, $10^{th}$ Edition, 1993, Luzán 5, S. A. de Ediciones.

In another particular embodiment, the composition of the invention is a cosmetic composition comprising at least one microparticle of the invention and/or a microparticle obtainable by means of the method of the invention, or a composition comprising a plurality of microparticles of the invention and/or of microparticles obtainable by means of the method of the invention. As used herein, the term "cosmetic composition" refers to a composition suitable for use in personal hygiene of human beings or animals, or in order to enhance the natural beauty or change the body appearance without affecting the structure or functions of the human or animal body, comprising one or more products providing such effects. If desired, the cosmetic composition provided by the invention can contain, in addition to the probiotic bacteria, one or more cosmetic products, i.e., substances or mixtures intended to be placed in contact with the external parts of the human or animal body (epidermis, hair system, nails, lips and external genital organs) or with the teeth and the buccal mucosa, for the exclusive or main purpose of cleaning them, perfuming them, changing their appearance, protecting them, keeping them in good condition or correcting body odors. Illustrative examples of cosmetic products include the products contained in the INCI (International Nomenclature of Cosmetic Ingredients) list.

In another particular embodiment, the composition of the invention is a cosmeceutical composition comprising at least one microparticle of the invention and/or a microparticle obtainable by means of the method of the invention, or a composition comprising a plurality of microparticles of the invention and/or of microparticles obtainable by means of the method of the invention. As used herein, the term "cosmeceutical composition" refers to a composition suitable for use in the body or animal body comprising one or more cosmeceutical products (functional cosmetics, dermoceuticals or active cosmetics), i.e., topical hybrid products with cosmetical-pharmaceutical characteristics containing active ingredients having effect on user's skin, hair and/or nails, at higher and more effective concentrations, therefore they are located in an intermediate level between cosmetic and drug. Illustrative examples of cosmeceutical products include essential oils, ceramides, enzymes, minerals, peptides, vitamins, etc. The person skilled in the art will understand that the microparticles of the invention or the compositions containing them can be part of a food or feed, or of a nutraceutical, pharmaceutical, or cosmeceutical product, which constitutes an additional aspect of the present invention. Said products can be in a liquid, semi-solid or solid form.

Additionally, the microparticles of the invention have a strong immunomodulatory effect and favor the induction of a Th1 response and/or shift the immune response towards Th1, preferably from Th2 towards Th1 (Example 7), they can therefore be used in the manufacture of an immune system modulating composition for the prevention and/or treatment of an immune system impairment, for example, in the prevention and/or treatment of Th2-mediated transplant rejection, allergies and allergy-associated diseases, immunodeficiencies and pathologies derived from said immunodeficiencies, infections caused by intracellular pathogens and/or mucosal infections.

Therefore in another aspect, the invention relates to the use of a microparticle of the invention, or of a composition of the invention, or of a food, pharmaceutical, cosmeceutical or nutraceutical product comprising at least one microparticle of the invention or said composition of the invention, hereinafter "product of the invention", in the manufacture of an immune system modulating composition. In other words, according to this inventive aspect the invention relates to a microparticle of the invention, or a composition of the invention, or a product of the invention for use in an immune system modulating composition.

As used herein, an "immune system modulating composition", hereinafter "immunomodulatory composition of the invention", is a composition which is capable of stimulating certain responses in the immune system, making it more reactive, for example, intervening in the development of the cells involved in immune response through the production of specific cytokines. As used herein, the term "composition" includes any pharmaceutical composition, food composition (food or feed), nutraceutical composition, etc., comprising the microparticle of the invention, the composition of the invention, or the product of the invention described above.

The results shown in the Example 7 clearly show that the oral administration of the microparticles of the invention containing $L.\ plantarum$ to CD1 mice, on one hand, induces a slight increase in the number of cytotoxic lymphocytes (clearly shown by a reduction in $CD4^+/CD8^+$ ratio) (FIG. 9), and, on the other hand, causes an increase in interferon-gamma (IFN-g) synthesis compared with the production of interleukin-6 (IL-6), thus shifting the immune response towards a Th1 profile. Although not wished to be bound thereto, these results seem to indicate a possible interaction between the microparticles of the invention and the immune system, modifying the type of immune response and shifting it towards a Th1 response.

Therefore in a particular embodiment, the immunomodulatory composition of the invention is a composition which preferably induces a Th1 response and/or shifts the immune response towards Th1, preferably from Th2 towards Th1. According to this particular embodiment, the immunomodulatory composition of the invention mainly or preferably stimulates or induces the Th1 response of the immune system making it more reactive through the production of specific cytokines, such as for example, IFN-g, interferon-alpha (IFN-a), interleukin-12 (IL-12), interleukin-18 (IL-18), etc., in the development of the cells involved in Th1 immune response. The person skilled in the art can easily determine if the administration of microparticles of the invention preferably induces a Th1 response and/or shifts the immune response from Th2 towards Th1 by means of conventional methods, for example, by means of methods based on quantifying specific cytokines of the Th1 response and optionally, Th2, such as for example, the assay described in Example 7.

In a preferred particular embodiment, the immunomodulatory composition of the invention is a composition suitable for oral administration (sometimes being referred to as "oral composition" in this description for the sake of simplicity) and will be presented in a solid, liquid or semi-solid dosage form. To that end, said immunomodulatory composition of the invention will include, together with the microparticles of the invention, or the composition of the invention, or the product of the invention, a pharmaceutically acceptable vehicle; said pharmaceutically acceptable vehicle comprises one or more excipients suitable for oral administration, for example, in the form of capsule, powder, granulate, suspension, etc. The person skilled in the art knows the excipients which are suitable for the formulation of pharmaceutical compositions intended for oral administration as well as the methods for producing said compositions. By way of illustration, information about excipients suitable for the formulation of compositions intended for oral administration, as well as about their production can be found in the book "Tratado de Farmacia Galénica", by C. Faulí i Trillo, 10$^{th}$ Edition, 1993, Luzán 5, S. A. de Ediciones.

In another particular embodiment, the immunomodulatory composition of the invention is an oral composition for the prevention and/or treatment of an immune system impairment; said immune system impairment can be a natural (genetic) impairment or an induced impairment, such as an impairment induced by an infectious process, stress, etc.

In another particular embodiment, the immunomodulatory composition of the invention is an oral composition for the prevention and/or treatment of:
- Th2 response-mediated transplant rejection,
- allergies and allergy-associated diseases,
- immunodeficiencies and pathologies derived from said immunodeficiencies,
- infections caused by intracellular pathogens, or
- mucosal infections.

Transplant rejection is a process in which the immune system of the transplant recipient attacks the transplanted organ or tissue. Due to their characteristics, the immunomodulatory composition of the invention can be particularly useful in the prevention and/or treatment of the Th2 response-mediated transplant (e.g., an organ, tissue, etc.) rejection.

Allergy is a hypersensitivity disorder of the immune system. Allergic reactions occur when the immune system of a person reacts to normally harmless substances in the environment. A substance causing an immune response (allergic reaction) in a subject sensitive to said substance is known as an "allergen". When an allergen enters the body of a subject who is allergic to it, the subject's immune system responds by producing a large amount of antibodies (IgE); successive exposure to the same allergen causes the release of chemical mediators, particularly histamine, which will produce the typical symptoms of an allergic reaction. There is a large variety of allergens, by way of non-limiting illustration, said allergens can be the allergenic extracts of pollens, the allergenic extracts of animals, including domestic animals, insects, mites, etc., the allergenic extracts of foods or food products, metals, components present in saliva, insect pincers or stingers inducing a sensitivity reaction in a subject, components present in plants inducing a sensitivity reaction in a subject, etc.

Among the most common allergies present in the population are:
- allergies to plant pollens, for example, allergies to *Gramineae* pollen (e.g., *Lolium perenne, Poa pratense, Phleum pratense, Cynodon dactylon, Festuca pratensis, Dactylis glomerata, Secale cereale, Hordeum vulgare, Avena sativa, Triticum sativa*, etc.), allergies to the pollen of other grasses (e.g., *Artemisia vulgaris, Chenopodium album, Plantago lanceolata, Taraxacum vulgare, Parietaria judaica, Salsola kali, Urtica dioica*, etc., allergies to tree pollen (e.g., *Olea Europea, Platanus* sp., *Cupresus* sp., etc.);
- allergies to animals, including, allergies to animal skin, dander or feathers (e.g., dog, cat, horse, poultry, etc.), allergies to insects, for example, allergy to the components present in insect saliva, pincers or stingers inducing a sensitivity reaction in a subject (e.g., bees, wasps, mosquitos, horseflies, etc.), allergies to mites, for example, dust mites (e.g., *Dermatophagoides pteronyssimus, Dermatophagoides farinae, Acaros Siro, Blomia tropicalis, Euroglyphus maynei, Glyciphagus domesticus, Lepidoglyphus destructor, Tyrophagus putrescentiae*, etc.);
- allergies to fungi (e.g., *Alternaria alternata, Cladosporium herbarum*, etc.);
- allergies to foods or food components present in foods, for example, fish, fruits (pineapple, kiwi, etc.);
- allergies to metals (e.g., nickel, etc.).

Generally, it is quite common that a subject who is sensitive to a specific allergen is also sensitive to other different allergens.

The immunomodulatory composition of the invention can be used orally for the prevention and/or treatment of allergies in general; in a particular embodiment, said allergy is selected from the group of allergies indicated above, i.e., from the group of allergies consisting of allergies to plant pollens, allergies to insects, allergies to mites, allergies to fungi; allergies to animals, allergies to food components present in foods, allergies to metals, allergies to dust, etc., and the combinations thereof.

Although it does not seem to be strictly necessary, in a particular embodiment, the prevention and/or the treatment of the allergies by means of using the immunomodulatory composition of the invention can be favored by the administration of the allergen causing the allergy. To that end, said allergen can be administered to the subject together with the immunomodulatory composition of the invention (simultaneous administration of the immunomodulatory composition of the invention and the allergen) by including the allergen in the formulation itself of the immunomodulatory composition of the invention or by administering the allergen in an independent formulation but simultaneously with the administration of the immunomodulatory composition of the invention. Alternatively, the allergen can be administered to the subject in a time period before or after the administration of the immunomodulatory composition of the invention (sequential administration of the immunomodulatory composition of the invention and the allergen); in this case, the allergen would be formulated in its own formulation. Although virtually any allergen can be administered, in this particular embodiment in a specific embodiment, said allergen is an allergen causing the allergies referred to in the preceding paragraphs. Said allergens can be obtained by conventional methods known by the persons skilled in the art or can be acquired on the market.

The immunomodulatory composition of the invention can be used orally for the prevention and/or treatment of allergy-associated diseases. The person skilled in the art knows the diseases generally associated with allergies. By way of non-limiting illustration, the most common allergy-associated diseases are selected from asthma and atopic dermatitis.

Immunodeficiency is a pathological state in which the capacity of the immune system to fight against infectious diseases is compromised or absent; under those conditions, the immune system does not fulfill its corresponding protective role, leaving the organism vulnerable to infection. In fact, immunodeficiencies make the affected people highly susceptible to infections. Generally, most immunodeficiencies are acquired immunodeficiencies ("secondary immunodeficiency"); nevertheless, some people are born with defects in their immune system ("primary immunodeficiency"). Transplant patients taking medicinal products to suppress their immune system as an anti-transplant rejection measure and patients having an over-active immune system are found among the subjects which may have immunodeficiency. Generally, people with immunodeficiency tend to be particularly vulnerable to opportunistic infections, in addition to the normal infections that could affect everyone.

Immunodeficiency can be physiological, congenital, or acquired immunodeficiency. Generally in an immunodeficiency situation, the organism defenses against pathogens decrease with the subsequent alteration of Th1/Th2 balance, such as for example, in physiological immunodeficiencies (e.g., in newborns, during pregnancy, etc.), primary or congenital immunodeficiencies (e.g., genetic diseases, such as for example, agammaglobulinemia in DiGeorge syndrome, etc.), or in acquired or secondary immunodeficiencies (e.g., immunodeficiencies acquired as a result of a malnutrition, aging, treatment with certain medicinal products, such as chemotherapeutic agents, antirheumatic agents, immunosuppressants (administered after organ transplant), glucocorticoids, etc.; Acquired Immunodeficiency Syndrome (AIDS), autoimmune diseases, etc.).

The immunomodulatory composition of the invention is useful for supporting the natural immune defenses of the organism, for example under specific stress conditions such as psychophysical stress which, if it is extremely intense or for a long period, can lead to an immunodeficiency situation clinically manifested through vulnerability to infections of variable intensity.

Since the immunomodulatory composition of the invention modulates the immune system preferably by inducing a Th1 response and/or shifting the immune response towards Th1 (for example from Th2 towards Th1), for example, it also can be used orally for the prevention and/or treatment of pathologies derived or resulting from immunodeficiencies. The person skilled in the art knows the pathologies derived from immunodeficiencies, for example, infections, etc.

Therefore, the immunomodulatory composition of the invention can be useful in the prevention and/or the treatment of immunodeficiencies of any origin and the resulting pathologies, for example, in the prevention and/or the treatment, orally, of infections caused by intracellular pathogens (e.g., bacteria, protozoa, virus, etc.) as well as mucosal infections (e.g., oral cavity infections, respiratory tract infections, gastrointestinal tract infections, urogenital tract infections, mucosal membrane infections, skin infections, etc.) and generally of all the infections derived from the immunodeficiency conditions.

In another particular embodiment, the immunomodulatory composition of the invention can be used in the treatment and/or prevention of infections caused by intracellular pathogens. In a particular embodiment, said intracellular pathogen is an eukaryotic pathogen, such as for example, a protozoon (e.g., *Plasmodium vivax* (which causes malaria), *Leishmania* sp. (associated with Leishmaniasis), *Entamoeba* sp., *Cryptosporidium* sp., etc. or a fungus, a prokaryotic pathogen, such as a bacterium (e.g., *Escherichia coli, Salmonella* sp., *Shigella* sp., *Campylobacter* sp., *Yersinia* sp., *Vibrio* sp., *Mycobacterium tuberculosis, M. leprae, Listeria* sp., *Brucella* sp., *chlamydias*, etc.,), or a virus (e.g., double-stranded DNA (dsDNA) virus, for example, adenovirus, herpesvirus, poxvirus, etc.), single-stranded DNA (ssDNA) virus, for example, parvovirus, etc., double-stranded RNA (dsRNA) virus, for example, reovirus, etc., positive single-stranded RNA ((+)ssRNA) virus, for example, picornavirus, togavirus, etc., negative single-stranded RNA [(−) ssRNA] virus, for example, orthomyxovirus, rhabdovirus, etc., reverse transcriptional single-stranded RNA (ssRNA-RT) virus, for example, retrovirus, etc.; or reverse transcriptional double-stranded RNA (dsRNA-RT) virus, for example, hepadnavirus, etc.).

In another particular embodiment, the immunomodulatory composition of the invention can be used in the treatment and/or prevention of mucosal infections; by way of non-limiting illustration, said mucosa can be oral cavity mucosa, gastrointestinal tract mucosa, urogenital tract mucosa and respiratory tract mucosa, etc. Generally, these infections can be caused by intracellular pathogens. In a particular embodiment, the mucosal infections are caused by enterobacteria (e.g., *Escherichia coli, Salmonella* sp., *Shigella* sp., *Campylobacter* sp., *Yersinia* sp., *Vibrio* sp., etc.), enterovirus (e.g., calicivirus, rotavirus, adenovirus, astrovirus, etc.) or protozoa (e.g., *Entamoeba* sp., *Cryptosporidium* sp., *Leishmania* sp., etc.).

The immunomodulatory composition of the invention preferably suitable for oral administration can be prepared by methods known by the persons skilled in the art taking into account the particular nature of the active ingredients present therein, which include living material, specifically probiotic bacteria, and preferably by the method provided by this invention since the microparticles thus produced protect said probiotic bacteria during processing, storage and administration, particularly during transit through the gastrointestinal tract (oral administration). Additionally, after being taken in, they facilitate probiotic bacteria release in the desired location, protecting them from the "acidic-peptic" conditions of the upper gastrointestinal tract, particularly of the stomach.

In a particular embodiment, the immunomodulatory composition of the invention is in a single dosage form for administration one or several times a day, according to the type and the severity of the pathology to be treated and the age and the weight of the subject.

In a particular embodiment, the microparticles of the invention present in the immunomodulatory composition of the invention are in the form of a dry powder or of a lyophilisate, optionally present in a vehicle suitable for administration to a subject. Generally, the active ingredients (microparticles, composition or product of the invention) are included in the suitable compositions.

Therefore in a particular embodiment, the immunomodulatory composition of the invention comprises a food, pharmaceutical or nutraceutical acceptable vehicle. In a specific embodiment, the pharmaceutical compositions, nutraceutical compositions or food products provided by this invention provide a suitable vehicle for the probiotic bacteria. Therefore in a specific embodiment, the immunomodulatory composition of the invention comprises a pharmaceutical composition, nutraceutical composition or is comprised in a food product. Non-limiting, illustrative examples include medicinal products, dietary products, products derived from milks, such as yoghurt, cheese, cream, confectioneries, fruit juices, etc., and can include, if desired as mentioned above, other substances beneficial for the organism, such as for example, vitamins, mineral salts, other compatible active ingredients, such as for example, prebiotic agents, fibers, etc.

As mentioned above, this inventive aspect can be alternatively expressed as a microparticle of the invention, or a composition of the invention, or a product of the invention for use in an immune system modulating composition (immunomodulatory composition of the invention). The characteristics of the immunomodulatory composition referred to above are herein applicable mutatis mutandi. In a preferred particular embodiment, said immune system modulating composition preferably induces a Th1 response and/or shifts the immune response towards Th1; preferably from Th2 towards Th1. Likewise, in a particular embodiment, said immune system modulating composition comprises a food, pharmaceutical or nutraceutical acceptable vehicle in addition to the microparticle of the invention, the composition of the invention, or the product of the invention. In another particular embodiment, said immune system modulating composition comprising microparticles of the invention, a composition of the invention, or a product of the invention, is in the form of a pharmaceutical composition, nutraceutical composition or is alternatively comprised in a food product. In another particular embodiment, the microparticles present in said immune system modulating composition are in the form of a dry powder.

The invention also relates to a microparticle of the invention, or a composition of the invention, or a product of the invention for being used orally in the prevention and/or the treatment of an immune system impairment (e.g., a natural impairment or an induced immune system impairment). In a particular embodiment, said microparticle of the invention is in a pharmaceutical composition formulated for oral administration. In another particular embodiment, said composition of the invention is a pharmaceutical composition formulated for oral administration. In another particular embodiment, said product of the invention is a pharmaceutical product suitable for oral administration.

Likewise, the invention also relates to a microparticle of the invention, a composition of the invention, or a product of the invention for being used orally in the prevention and/or the treatment of Th2-mediated transplant rejection; allergies and allergy-associated diseases; immunodeficiencies and pathologies derived from said immunodeficiencies; infections caused by intracellular pathogens, or mucosal infections [the characteristics of the Th2-mediated transplant rejection, allergies and allergy-associated diseases; immunodeficiencies and pathologies derived from said immunodeficiencies; infections caused by intracellular pathogens, or mucosal infections have already been mentioned above and are incorporated by reference]. In a particular embodiment, said microparticle of the invention is in a pharmaceutical composition formulated for oral administration. In another particular embodiment, said composition of the invention is a pharmaceutical composition formulated for oral administration. In another particular embodiment, said product of the invention is a pharmaceutical product suitable for oral administration.

In another aspect, the invention relates to a method for the prevention and treatment of an immune system impairment or pathology in a subject, which comprises orally administering to a subject in need of treatment, an effective amount of an immunomodulatory composition of the invention, or of microparticles of the invention, or of a composition of the invention, or of a product of the invention.

As used herein, the term "immune system impairment or pathology" in a subject comprises both natural and induced immune system impairments, such as diseases in which a Th-1 response-based treatment may be beneficial, for example, Th2-mediated transplant rejection; allergies and allergy-associated diseases; immunodeficiencies and pathologies derived from said immunodeficiencies; infections caused by intracellular pathogens, or mucosal infections. The characteristics of the Th2-mediated transplant rejection, allergies and allergy-associated diseases; immunodeficiencies and pathologies derived from said immunodeficiencies; infections caused by intracellular pathogens, or mucosal infections have already been mentioned above and are incorporated by reference.

As used herein, the term "subject" includes any mammal animal including human being.

The characteristics of the immunomodulatory composition of the invention, the microparticles of the invention, the composition of the invention, or the product of the invention have already been defined above and are incorporated herein by reference.

The characteristics of the presentation and administration form of the immunomodulatory composition of the invention, the microparticles of the invention, the composition of the invention, or the product of the invention have already been mentioned above and are incorporated by reference.

For administration to the subject in need of treatment, the immunomodulatory composition of the invention, the microparticles of the invention, the composition of the invention, or the product of the invention can be included in a food, pharmaceutical or nutraceutical acceptable vehicle, or can be present in a pharmaceutical composition, nutraceutical composition or comprised in a food product.

The following examples illustrate the invention and must not be considered as limiting same.

EXAMPLES

The following examples describe the production of casein and chitosan microparticles which can incorporate probiotic bacteria and which are capable of protecting said microorganisms from the aforementioned factors (processing, storage and/or transit through the gastrointestinal tract). Unless otherwise indicated, the general methods used are described below for carrying out these examples.

General Methods

I. General Method for Producing Empty Casein and Chitosan Microparticles

The method for producing casein and chitosan microparticles comprises dissolving sodium caseinate (ANVISA, Madrid, Spain) in an aqueous medium followed by adding a specific volume of chitosan solution and optionally a specific amount of cross-linking agent under magnetic stirring and with constant flow. The microparticles formed are dried after the suspension containing them goes through a spray-dryer after the addition of a protective agent such as mannitol.

Unless otherwise indicated, the chitosan used in these examples was Characterized Chitosan with a degree of deacetylation of 90.2% and a molecular weight of 105±0.01 kDa, from Guinama (Valencia, Spain).

Unless otherwise indicated, the spray-dryer used in these examples was the Büchi B-290 Mini Spray-Dryer with Büchi accessories, B-295 Inert Loop and B-296 Dehumidifier, Büchi Switzerland, Flawil (Switzerland).

The mannitol used in these examples was D-mannitol, E-421, of 99.4% purity from Guinama (Valencia, Spain), although D-mannitol from Sigma-Aldrich was also used sometimes.

II. Microparticle Characterization

The size of the microparticles was determined by means of light microscopy using an Olympus CH40 microscope with Colorview Soft Imaging Systems camera.

The morphology of the microparticles was further observed using scanning electron microscopy (Zeiss, DSM 940A, Germany). To that end, the microparticles were coated with a layer of molecular gold of 9 nm (Emitech K550, Sputter-Coater equipment, United Kingdom) and the photographs were taken with a Zeiss DMS 940 A microscope (United States).

III. General Method for Preparing the Suspensions of Probiotic Bacteria

The probiotic bacteria used for carrying out these examples were *Lactobacillus plantarum* CECT 220 and *Lactobacillus casei* CECT 475 T isolated from corn silage and cheese, respectively. The freeze-dried products of both microorganisms were revitalized in an MRS broth (Merck, Barcelona) at 37° C. under anaerobic atmosphere (85% nitrogen, 10% hydrogen, 5% carbon dioxide) in anaerobic chamber (MACS 500 AIRLOCK, AES Chemunex, Spain). 500 μL aliquots of stock suspensions which were kept frozen at −85° C. until the time of use were prepared from these revitalized cultures.

The working suspensions were prepared as follows. 100 μL of the aliquot of the corresponding microorganism were transferred to 10 mL MRS broth. After incubation for 12 hours/37° C. under anaerobic conditions, the microscopic count was performed in a Thoma chamber in order to calculate the volume of sample that must be transferred to a 50 mL flask containing the MRS broth to reach a count of $10^6$ CFU/mL (colony forming units per milliliter). After inoculating that volume, the flasks were incubated in the previously described conditions for 24 hours until reaching the early stationary growth phase. The bacterial population was tracked and counted by means of seeding the corresponding decimal dilutions (0.1% BPW broth (Merck, Barcelona)) in MRS agar (Merck, Barcelona) at each sampling time.

IV. General Method for Producing Casein and Chitosan Microparticles Containing Encapsulated Probiotic Bacteria The general method for producing casein and chitosan microparticles containing encapsulated probiotic bacteria comprises dissolving sodium caseinate (ANVISA, Madrid, Spain) in an aqueous medium followed by adding a specific volume of bacterial suspension obtained according to the method described in Section III above and after being centrifuged and resuspended in a specific volume of a solution of 2% sucrose (w/v), under stirring and with constant flow. A specific volume of chitosan solution and optionally a specific volume of cross-linking agent are then added.

V. General Method for Staining the Probiotic Bacteria and the Encapsulation Thereof This method was carried out for qualitatively confirming that the bacteria are trapped inside the microparticles, i.e., that the matrix consisting in casein and chitosan coats the probiotic bacteria, through fluorescence light microscopy.

The method for staining the bacteria comprises preparing a saturated solution of rhodamine B isothiocyanate in phosphate buffer (pH 7.4), filtering it through a 0.2 μm membrane and adding it to a specific volume of bacterial suspension obtained according to the method described in the preceding sections. Once the mixture is centrifuged at 3,000 rpm for 15 minutes to remove the rhodamine excess in the supernatant, the stained bacteria are resuspended in a specific volume of a solution of 2% sucrose (w/v). The stained bacteria are encapsulated according to the method described in the preceding section.

VI. General Method for Quantifying Viable Bacteria Present in the Formulation, and Determining the Bacterial Death Cycle Throughout the Process To count the encapsulated bacteria, 1 mL of a solution of 1% NaOH (pH 10) was added to a known weight of microcapsules (500 μg approximately), and after vortexing for 5 minutes the corresponding decimal dilutions were performed in 0.1% BPW broth (Merck, Barcelona, Spain) and seeded in an MRS agar plate. After incubation at 37° C. under anaerobic conditions (MACS 500 Airlock chamber, AES Chemunex, Spain) for 24-48 hours, colony counts were performed.

Taking into account the amount of bacteria initially included in the formulation before them going through the spray-dryer per each gram of formulation and the counts obtained at the end of the process, the bacterial death cycles are determined by means of the following equation:

Bacterial death cycles: log(initial CFU/g)−log(recovered CFU/g)

VII. Method for Evaluating the Resistance of Microencapsulated Lactic Bacteria in Simulated Gastrointestinal Medium The gastrointestinal resistance of *L. plantarum* and *L. casei* was evaluated according to the method described by Vinderola et al., 2003.

To conduct the study, 10 μL of the liquid bacterial culture or 500 μg of the formulation of microparticles in the form of powder were added to PVC tubes with 0.99 mL of gastric simulant at pH 2.5. As many tubes were used as treatment times planned to be evaluated, specifically 5 tubes with gastric simulant corresponding to the times: 0 and 2 hours (resistance to gastric simulant)) and 0, 3 and 6 hours (resistance to intestinal simulant).

The gastric simulant was prepared according to pharmacopeia and had the following composition for 1 liter of solution:
 2 g NaCl
 3.2 g pepsin (Sigma, Barcelona, Spain)
 7 mL 37% HCl(v/v)

The pepsin was dissolved in HCl and the mixture was then added to 1 liter of type I water. The final pH was adjusted to 1.2 or 2.5 depending on the test to be conducted with 37% HCl (v/v).

The intestinal simulant also prepared from pharmacopeia recipe was made up of:
 6.8 g monobasic potassium phosphate (Panreac, Madrid, Spain) dissolved in 250 mL of type I water and to which 77 mL of 0.2 N NaOH were added
 500 mL water
 10 g pancreatin (Sigma, Barcelona, Spain)

The pH was adjusted to 6.8 with 0.2 N NaOH or with 0.2 N HCl.

The 5 tubes were kept at 37° C. in an orbital stirrer (150 rpm) until the time of sample extraction and survivor evaluation. After the time of treatment in gastric simulant (2 hours) has lapsed, the PVC tubes were centrifuged (13,000 rpm/10 minutes) and the supernatant was discarded. To evaluate the time of 2 hours, the pellet of one of the tubes was subjected to a treatment for rupturing the microcapsules with 1% NaOH (pH 10) described above. The pellets of the remaining tubes were resuspended in 0.99 mL of intestinal simulant to evaluate the resistance in this medium at times of 0, 3 and 6 hours (2, 5 and 8 hours from the start of the study). After those times have lapsed, the tubes were centrifuged, the supernatants were discarded and the pellets were treated with 1% NaOH (treatment for rupturing the microcapsules) in order to evaluate the remaining survivors.

The viable bacteria count was performed using the method of counting in an MRS agar plate described above. The plates were incubated at 37° C. for 24 to 48 hours under anaerobic conditions determining the number of colony forming units. The fraction of surviving bacteria was calculated according to the following equation:

$$\text{Log survivor fraction} = \text{Log}\left(\frac{N_t}{N_0}\right)$$

where $N_t$ represents the total viable lactic acid bacteria after each time of treatment, and $N_0$ represents the initial number of inoculated lactic acid bacteria (LAB) (Bao et al., 2010).

VIII. Method for Evaluating the Stability of Microencapsulated Lactic Bacteria Over Storage Time Under Environmental Conditions Microencapsulated bacteria stability study was conducted by means of evaluating the bacterial viability over storage time at room temperature (25° C.)

To that end, 500 μg of samples were taken from the formulations of microcapsules kept in hermetically sealed glass container, said samples were subjected to the rupturing and survivor evaluation method described above. As a control, the study was conducted in a similar manner both in fresh suspensions and in freeze-dried products of both microorganisms.

Example 1

Preparation and Characterization of Casein and Chitosan Microparticles Containing Encapsulated Probiotic Bacteria of the Genus *Lactobacillus plantarum*

Different types of microparticles containing bacteria were prepared, all of them with casein as the base polymer modified with chitosan. The method for preparing said microparticles depended on the presence or absence of cross-linking agent and on the type of cross-linking agent used.

(Ap) Casein Microparticles Modified with Chitosan in the Absence of Cross-Linking Agent 1.5 mL of the bacterial suspension ($1.2 \times 10^{12}$ CFU/mL) described in Section III of the "General Methods" were added to 25 mL of a 10 mg/mL aqueous solution of sodium caseinate after being centrifuged and resuspended in a solution of 2% sucrose (w/v). 10 mL of a chitosan solution having a concentration of 1.6 mg/mL prepared in an aqueous medium with pH 5.5-6 by means of adding 400 mg of chitosan to 250 ml of purified water under stirring and adjusting the pH with 0.1 N HCl, were then added to the mixture.

After five minutes of incubation, 100 mg of mannitol were added to the preceding mixture and the formulation was then dried using the spray-drying technique. The processing conditions were:
Air inlet temperature: 85° C.
Air outlet temperature: 40-45° C.
Air pressure: 6 bar ($6 \times 10^5$ Pa)
Sample pumping rate: 3.5 mL/min
Suction: 100%
Airflow: 600 L/h The microparticles obtained in the form of powder were again collected for characterization and quantification. The same study was conducted in the absence of bacteria to check how the presence of these probiotics affects the physicochemical characteristics of the particles. FIG. 1 shows the light microscopy images obtained for the particles, both in the presence and in the absence of probiotics. It can be confirmed in the images that the particle size is not affected by the presence of encapsulated bacteria.

Figure 2:
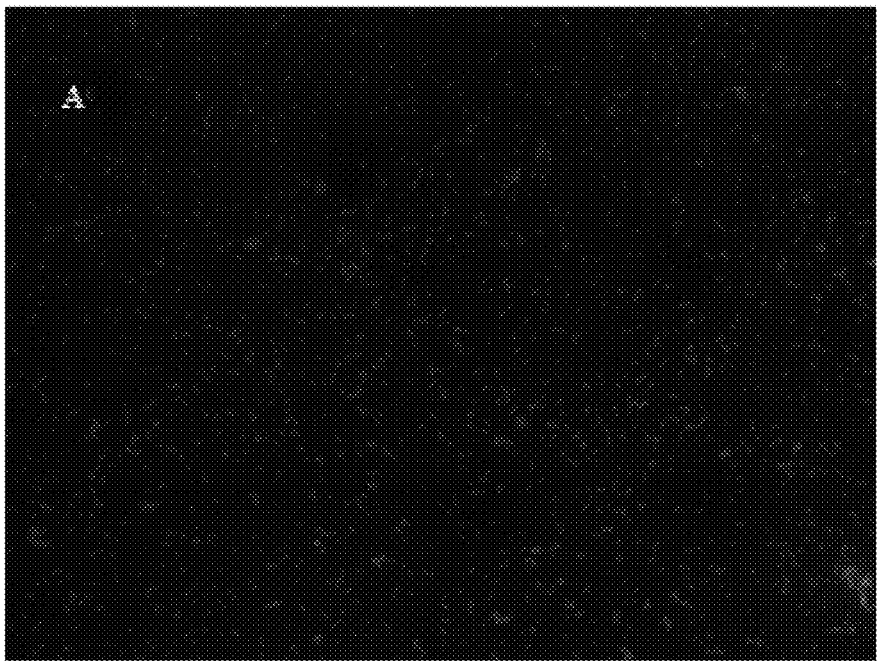
FIG. 2 shows the fluorescence light microscopy images of: A) $L.$ $plantarum$ stained with fluorescent marker (×20); B) casein microparticles modified with chitosan obtained by means of spray-drying with encapsulated (×20) $L.$ $plantarum$ (stained with fluorescent marker). The horizontal line in the lower right part represents 100 μm.
Figure 2:
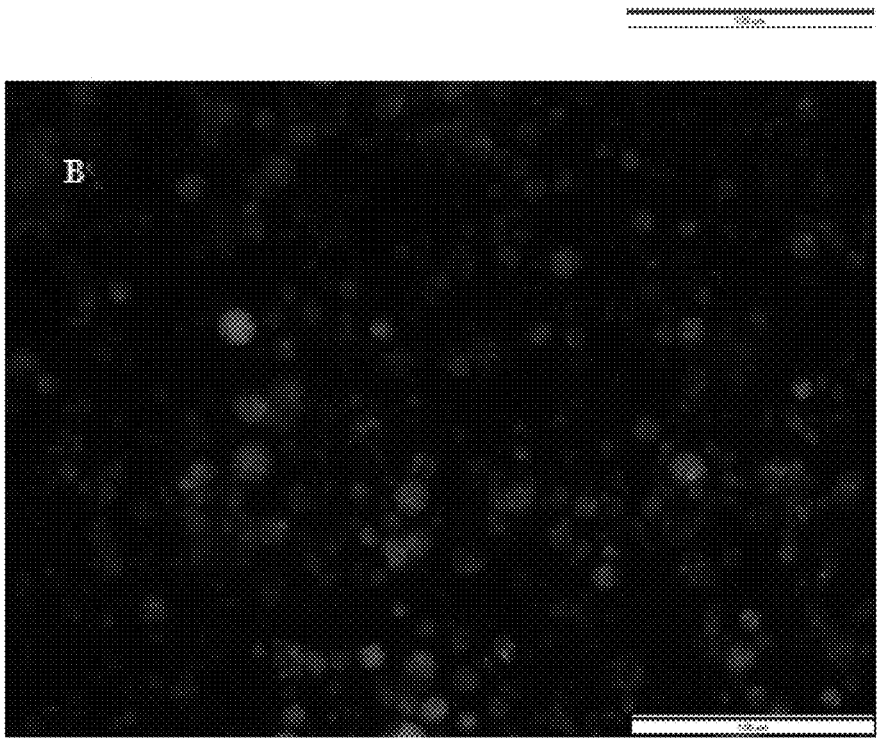

On the other hand, in order to confirm that the bacteria are encapsulated in the casein and chitosan microparticles, the same study was repeated using bacteria stained with fluorescent marker according to the method described in Section V of the "General Methods". FIG. 2 shows the fluorescence light microscopy images of both the stained free bacteria (A) and encapsulated bacteria (B). The fluorescence observed in the microparticles (A) is due exclusively to the bacteria. Since the presence of bacteria outside the microparticles is not observed at all, it is confirmed that they are encapsulated.

(Bp) Casein and Chitosan Microparticles in the Presence of Vanillin 0.5 mL of an aqueous solution of vanillin (5 mg/mL) were added to 25 mL of a 10 mg/mL aqueous solution of sodium caseinate. After (at least) 15 minutes of incubation, 0.3 mL of the bacterial suspension ($4.7 \times 10^{11}$ CFU/mL) described in Section III of the "General Methods" were added to the mixture, after being centrifuged and resuspended in a solution of 2% sucrose (w/v). 10 mL of a chitosan solution having a concentration of 1.6 mg/mL prepared in an aqueous medium with pH 5.5-6 were then added to the mixture.

After five minutes of incubation, 250 mg of mannitol were added to the preceding mixture and the formulation was then dried using the spray-drying technique. The processing conditions were similar to those described in Section Ap.

The microparticles obtained in the form of powder were again collected for characterization and quantification.

(Cp) Casein and Chitosan Microparticles in the Presence of TPP 1.5 mL of the bacterial suspension ($4.7 \times 10^{11}$ CFU/mL) described in Section III of the "General Methods" were added to 25 mL of a 10 mg/mL aqueous solution of sodium caseinate, after being centrifuged and resuspended in a solution of 2% sucrose (w/v). 10 mL of a chitosan solution having a concentration of 1.6 mg/mL prepared in an aqueous medium with pH 5.5-6 were then added to the mixture. After five minutes of incubation, 0.8 mL of a 1 mg/mL solution of TPP were added.

250 mg of mannitol were added five minutes later to the preceding mixture and the formulation was then dried using the spray-drying technique. The processing conditions were similar to those described in Section Ap.

The microparticles obtained in the form of powder were again collected for characterization and quantification.

(Dp) Casein and Chitosan Microparticles in the Presence of Calcium Salts 4 mL of the bacterial suspension ($1.2 \times 10^{12}$ CFU/mL) described in Section III of the "General Methods" were added to 25 mL of a 10 mg/mL aqueous solution of sodium caseinate, after being centrifuged and resuspended in a solution of 2% sucrose (w/v). 2 mL of a chitosan solution having a concentration of 1.6 mg/mL prepared in an aqueous medium with pH 5.5-6 were then added to the mixture. After five minutes of incubation, 2 mL of a solution of 2% calcium acetate (w/v) and 2 mL of a solution of 2% calcium chloride (w/v) were added.

100 mg of mannitol were added five minutes later to the preceding mixture and the formulation was then dried using the spray-drying technique. The processing conditions were similar to those described in Section Ap.

The microparticles obtained in the form of powder were again collected for characterization and quantification.

Figure 3:
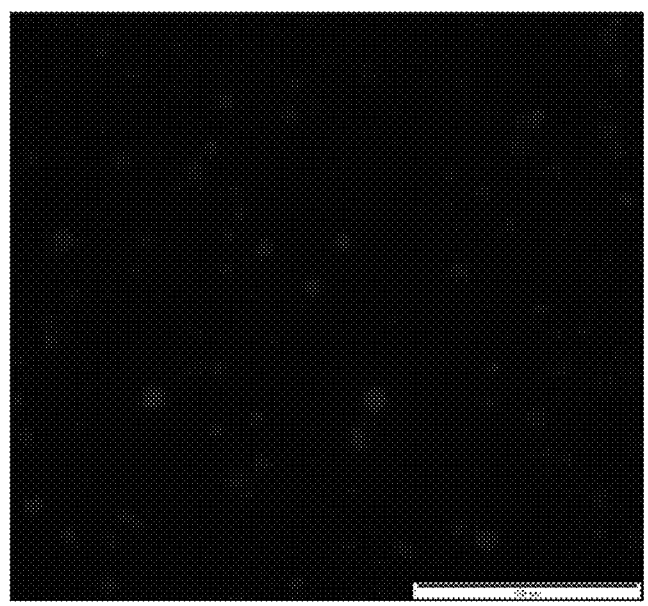
FIG. 3 shows the fluorescence light microscopy image of casein microparticles modified with chitosan and in the presence of calcium salts obtained by means of spray-drying with encapsulated (×20) $L.$ $plantarum$ (stained with fluorescent marker). The horizontal line in the lower right part represents 100 μm.

FIG. 3 shows the fluorescence light microscopy image obtained for the microparticles, in which the presence of free bacteria is not observed.

Table 1 summarizes the death cycles of *L. plantarum* which are derived from the process of encapsulation in casein and chitosan microparticles.

TABLE 1

Influence of casein microparticle production method on
*Lactobacillus plantarum* survival

| Formulation Type | Bacteria count before drying by SD (CFU/g) | Bacteria count after drying by SD (CFU/g) | Bacterial death cycles due to the process for obtaining the microparticles (log CFU) |
|---|---|---|---|
| Ap | $3.67 \times 10^{12}$ | $2.50 \times 10^{10}$ | 2.17 |
| Bp | $2.42 \times 10^{11}$ | $2.50 \times 10^{10}$ | 0.99 |
| Cp | $1.21 \times 10^{12}$ | $7.50 \times 10^{10}$ | 1.21 |
| Dp | $9.28 \times 10^{12}$ | $1.70 \times 10^{10}$ | 2.74 |

SD: spray-drying

The sizes of the obtained microparticles are similar in all the formulations ranging about 7±4 μm. However, the bacterial death cycles are lower when vanillin or TPP is used as cross-linking agents.

According to the obtained results, the formulations Bp and Cp are those which offer better protection to the probiotics during the process for obtaining same. Therefore, both formulations were chosen to perform studies on gastrointestinal resistance and viability during storage.

Example 2

Figure 4:
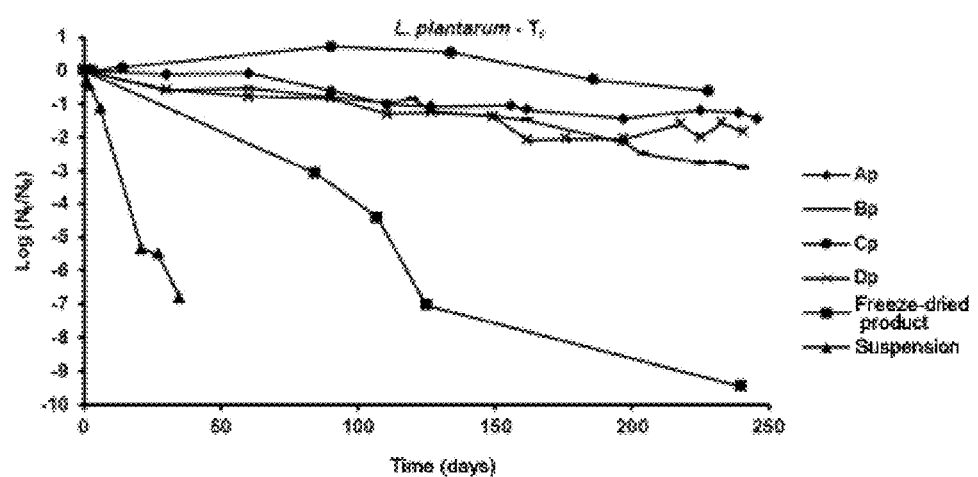
FIG. 4 is a graph showing the survival of $L.$ $plantarum$ under environmental conditions (25° C.) over time: fresh suspension of $L.$ $plantarum$; non-encapsulated lyophilized $L.$ $plantarum$; $L.$ $plantarum$ encapsulated in casein microparticles modified with chitosan (formulation Ap); $L.$ $plantarum$ encapsulated in casein microparticles modified with chitosan in the presence of vanillin (formulation Bp); $L.$ $plantarum$ encapsulated in casein microparticles modified with chitosan in the presence of TPP (formulation Cp); and $L.$ $plantarum$ encapsulated in casein microparticles modified with chitosan in the presence of calcium salts (formulation Dp).

Evaluation of the Stability of Encapsulated *Lactobacillus plantarum* Over Storage Time Under Environmental Conditions The formulations Ap, Bp, Cp and Dp described in Example 1 were used to evaluate the survival of the bacteria under environmental conditions (25° C.) over time, using both fresh suspensions and freeze-dried products as a comparative control. FIG. 4 shows the obtained results.

The results clearly show that in the first month of study there is a loss of 7 logarithmic units in the counts of fresh bacteria in suspension, and in the third month, losses of 4.5 logarithmic units were observed in the case of bacteria in lyophilized form. However, when these probiotics were encapsulated in any of the casein and chitosan microparticles described in Example 1, their counts were kept constant, no significant losses being observed during the 8 months of study. These results confirm that the formulations described in the present invention allow at least increasing the bacterial viability under environmental conditions by two fold with respect to the lyophilized bacteria.

Example 3

Figure 5:
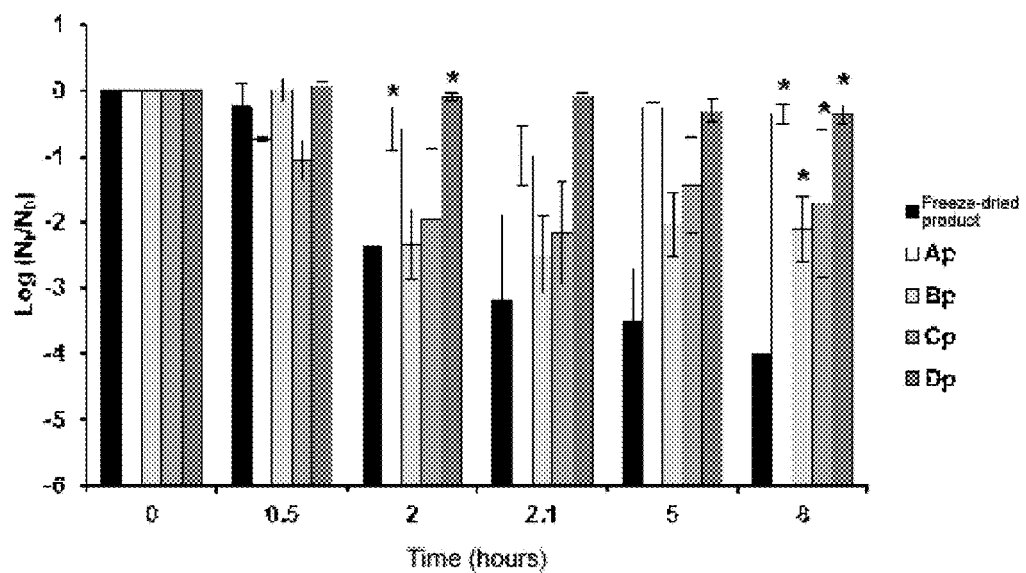
FIG. 5 is a graph showing the survival of $L.$ $plantarum$ in simulated gastrointestinal medium (0 to 2 hours: simulated gastric medium; 2.1 to 8 hours: simulated intestinal medium): fresh suspension of $L.$ $plantarum$; non-encapsulated lyophilized $L.$ $plantarum$; $L.$ $plantarum$ encapsulated in casein microparticles modified with chitosan (formulation Ap); $L.$ $plantarum$ encapsulated in casein microparticles modified with chitosan in the presence of vanillin (formulation Bp); $L.$ $plantarum$ encapsulated in casein microparticles modified with chitosan in the presence of TPP (formulation Cp); and $L.$ $plantarum$ encapsulated in casein microparticles modified with chitosan in the presence of calcium salts (formulation Dp). * indicates significant differences in the microparticle counts with respect to the freeze-dried product ($p<0.05$).

Evaluation of the Resistance of the Encapsulated Probiotic Bacteria of the Genus *Lactobacillus plantarum* to Simulated Gastrointestinal Medium The formulations Ap, Bp, Cp and Dp described in Example 1 were used to evaluate the resistance of the encapsulated bacteria in a simulated gastrointestinal medium following the method described in Section VII of the "General Methods". FIG. 5 shows the results obtained for both formulations throughout the process, as well as the resistance obtained for free non-encapsulated bacteria. In the case of free bacteria (non-encapsulated lyophilized bacteria), the number of viable counts decrease gradually throughout the study ending with a mean loss of 4 logarithmic units. In the case of formulations Ap and Dp, the counts were kept virtually constant throughout the entire assay, being significantly higher than the freeze-dried product both at the end of the assay in gastric simulant (2 hours) and at the end of the assay in intestinal simulant (8 hours). In formulations Bp and Cp a decrease in the concentration was observed during the residence in gastric simulant, the counts at the time of 2 hours being significantly similar to the freeze-dried product. However, once the microparticles are transferred to the intestinal simulant, an increase in the counts was observed, being significantly higher than the freeze-dried product at the end of the assay (8 hours). This increase in the final counts has been previously described by other authors in studies conducted with *bifidobacteria*, in which they conclude that the phenomenon is due to the fact the damage experienced by the bacteria during low pH stress is only temporary, and does not end up killing the bacteria, which allows them to recover when passed to an intestinal medium (Lacroix and Picot, 2004).

In summary, after the study in the gastric simulant medium (2 hours), higher survivals were observed when the bacteria were encapsulated in formulations Ap and Dp than when they were free, said differences being significant. In contrast, these differences were not observed in formulations Bp and Cp. However, after ending the study (after 8 hours, after passage through the gastric simulant medium and then the simulated intestinal medium), the differences were greater and significant for all the formulations of microparticles (Ap, Bp, Cp and Dp), reaching a difference of up to three cycles with respect to the freeze-dried product.

These results demonstrate that the microparticles described significantly increase the tolerance of the studied bacteria to simulated gastrointestinal conditions.

Figure 6:
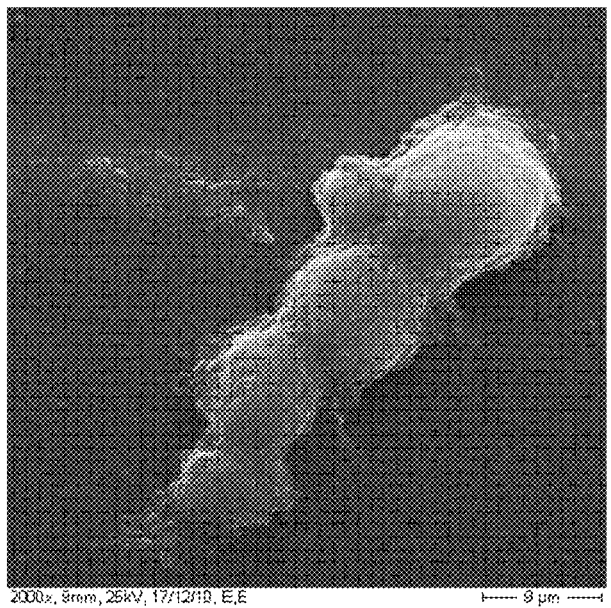
FIG. 6 shows the scanning electron microscopy images showing casein microparticles modified with chitosan in the presence of vanillin (formulation Bp), during degradation process with encapsulated $L.$ $plantarum$, after being subjected to treatment in simulated gastrointestinal medium.
Figure 6:
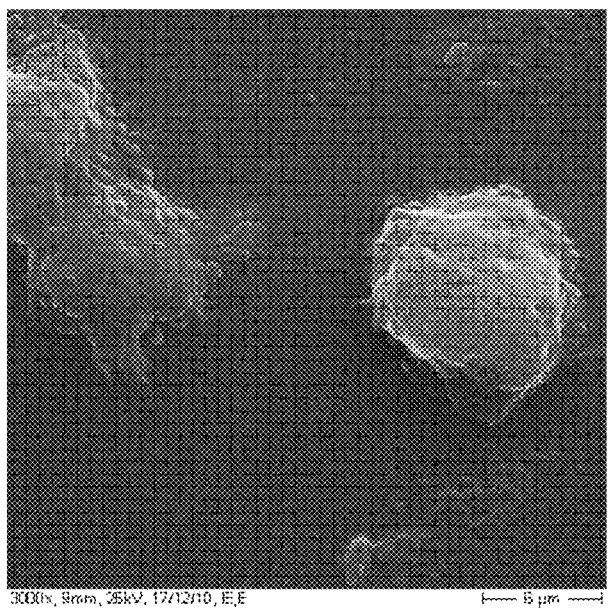

On the other hand, the microparticles were characterized for evaluating their state during the degradation process over time. FIG. 6 allows observing that the bacteria are housed inside the microparticles and are released to the medium when said microparticles are degraded over time.

Example 4

Preparation and Characterization of Casein Microparticles or of Casein and Chitosan Microparticles Containing Encapsulated Probiotic Bacteria of the Genus *Lactobacillus casei*

Different types of microparticles containing bacteria were prepared, all of them with casein as the base polymer and chitosan. The method for preparing said microparticles depended on the type of cross-linking agent used.

(Ac) Casein Microparticles Modified with Chitosan in the Absence of Cross-Linking Agent 2 mL of the bacterial suspension ($2.2 \times 10^{10}$ CFU/mL) described in Section III of the "General Methods" were added to 25 mL of a 10 mg/mL aqueous solution of sodium caseinate, after being centrifuged and resuspended in a solution of 2% sucrose (w/v). 10 mL of a chitosan solution having a concentration of 1.6 mg/mL prepared in an aqueous medium with pH 5.5-6 by means of adding 400 mg of chitosan to 250 ml of purified water under stirring and adjusting the pH with 0.1 N HCl, were then added to the mixture. After five minutes of incubation, 100 mg of mannitol were added to the preceding mixture and the formulation was then dried using the spray-drying technique. The processing conditions were:
  Air inlet temperature: 85° C.
  Air outlet temperature: 40-45° C.
  Air pressure: 6 bar ($6 \times 10^5$ Pa)
  Sample pumping rate: 3.5 mL/min
  Suction: 100%
  Airflow: 600 L/h The microparticles obtained in the form of powder were again collected for characterization and quantification. The same study was conducted in the absence of bacteria to check how the presence of these probiotics affects the physicochemical characteristics of the particles.

(Bc) Casein and Chitosan Microparticles in the Presence of Calcium Salts 1.8 mL of the bacterial suspension ($9.4 \times 10^{10}$ CFU/mL) described in Section III of the "General Methods" were added to 150 ml of a 10 mg/mL aqueous solution of sodium caseinate, after being centrifuged and resuspended in a solution of 2% sucrose (w/v). 25.5 mL of a chitosan solution having a concentration of 1.6 mg/mL prepared in an aqueous medium with pH 5.5-6 were then added to the mixture. A mixture of calcium salts (12 ml of 2% calcium acetate w/v and 12 ml of 0.9% calcium chloride w/v) was added to this solution.

After five minutes of incubation, 1,500 mg of mannitol were added to the preceding mixture and the formulation was then dried using the spray-drying technique. The processing conditions were the following:

Air inlet temperature: 75° C.
Air outlet temperature: 38° C.
Air pressure: 6 bar ($6 \times 10^5$ Pa)
Sample pumping rate: 3.5 mL/min
Suction: 100%
Airflow: 600 L/h The microparticles obtained in the form of powder were again collected for characterization and quantification.

(Cc) Casein and Chitosan Microparticles Cross-Linked with Vanillin 0.5 mL of an aqueous solution of vanillin (5 mg/mL) were added to 25 ml of a 10 mg/mL aqueous solution of sodium caseinate. After (at least) 15 minutes of incubation, 3 mL of the bacterial suspension ($1.2 \times 10^9$ CFU/mL) described in Section III of the "General Methods" were added to the mixture, after being centrifuged and resuspended in a solution of 2% sucrose (w/v). 10 mL of a chitosan solution having a concentration of 1.6 mg/mL prepared in an aqueous medium with pH 5.5-6 were then added to the mixture.

After five minutes of incubation, 200 mg of mannitol were added to the preceding mixture and the formulation was then dried using the spray-drying technique. The processing conditions were similar to those described in Section Bc.

The microparticles obtained in the form of powder were again collected for characterization and quantification.

(Dc) Casein and Chitosan Microparticles Cross-Linked with Tripolyphosphate 1.2 mL of the bacterial suspension ($9.4 \times 10^{10}$ CFU/mL) described in Section III of the "General Methods" were added to 100 ml of a 10 mg/mL aqueous solution of caseinate, after being centrifuged and resuspended in a solution of 2% sucrose (w/v). 20 mL of a chitosan solution having a concentration of 1.6 mg/mL prepared in an aqueous medium with pH 5.5-6 were then added to the mixture. 1.6 mL of TPP (1 mg/ml) were added thereto.

After five minutes of incubation, 1,000 mg of mannitol were added to the preceding mixture and the formulation was then dried using the spray-drying technique. The processing conditions were similar to those described in Section Bc.

The microparticles obtained in the form of powder were again collected for characterization and quantification.

Table 2 summarizes the physicochemical characteristics of the casein and chitosan microparticles containing encapsulated *L. casei*, as well as the bacterial death cycles derived from the particle production process.

TABLE 2

Physicochemical characteristics of the casein and chitosan microparticles with encapsulated *Lactobacillus casei*.

| Formulation Type | Bacteria count before drying by SD (CFU/g) | Bacteria count after drying by SD (CFU/g) | Bacterial death cycles due to the process for obtaining the microparticles (log CFU) |
|---|---|---|---|
| Bc | $4.49 \times 10^{10}$ | $3.80 \times 10^9$ | 1.07 |
| Cc | $6.82 \times 10^9$ | $7.80 \times 10^9$ | 0.00 |
| Dc | $4.89 \times 10^{10}$ | $1.30 \times 10^{10}$ | 0.58 |

SD: spray-drying

The sizes of the obtained microparticles are similar in all the cases ranging about 7±4 µm. Regarding the production process, the data show that the developed formulations generally protect *L. casei* better than *L. plantarum* throughout the process and furthermore, the formulations Cc and Dc are those that confer best protection.

Although there is no consensus regarding the minimum count of viable probiotics per gram or milliliter of product, concentrations in the order of $10^7$-$10^8$ CFU/mL (CFU/g) at the end of its shelf life have been generally accepted as the minimum satisfactory level. It has also been established that the probiotic products must be consumed regularly in amounts of about 100 g/day so that counts of $10^9$ cfu are released into the intestine (Karimi et al., 2011; Mohammadi et al., 2011; Vinderola et al., 2000a). Therefore, the method provided by the present invention can be considered as a suitable method since it maintains bacterial counts in the order of $10^9$ CFU/g (Table 2), which allows its formulation in foods with proportions in the order of 1%, maintaining the necessary concentration of probiotic bacteria of $10^7$ CFU/g, for example.

In order to know the gastrointestinal resistance and viability of the encapsulated bacteria during storage, formulations Cc and Dc were chosen since they provided the best protection results and do not require using high pressures, simplifying the production process.

Example 5

Figure 7:
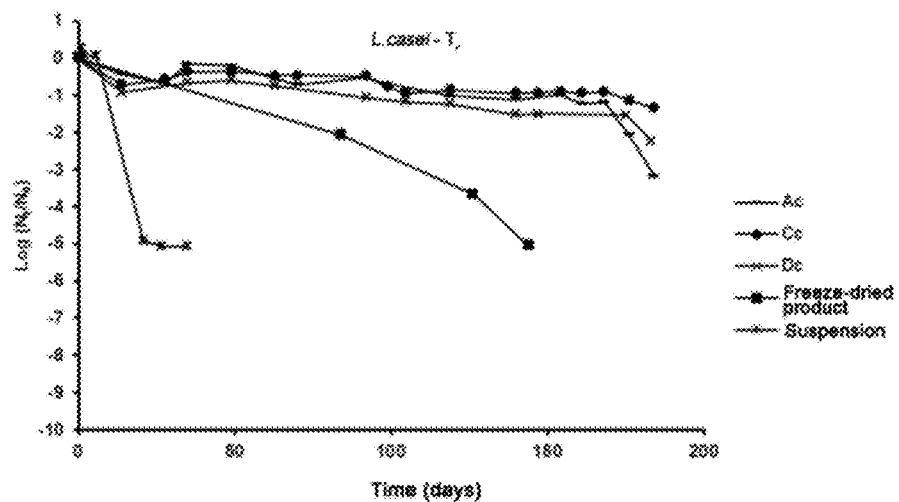
FIG. 7 is a graph showing the survival of $L.$ $casei$ under environmental conditions (25° C.) over time: fresh suspension of $L.$ $casei$; non-encapsulated lyophilized $L.$ $casei$; $L.$ $casei$ encapsulated in casein microparticles modified with chitosan (formulation Ac); $L.$ $casei$ encapsulated in casein microparticles modified with chitosan in the presence of vanillin (formulation Cc); and *L. casei* encapsulated in casein microparticles modified with chitosan in the presence of tripolyphosphate (TPP) (formulation Dc).

Evaluation of the Stability of Encapsulated *Lactobacillus casei* Over Storage Time Under Environmental Conditions Formulations Ac, Cc and Dc described in Example 4 were used to evaluate the survival of the bacteria under environmental conditions over time using both fresh suspensions and freeze-dried products as a comparative control. FIG. 7 summarizes the obtained results.

The results shows that in the first month of study there is a loss of 5 logarithmic units in the counts of fresh bacteria in suspension, and in the third month, losses of 3 logarithmic units were observed in the case of lyophilized bacteria, loss of 5 logarithmic units being reached in the fifth month. In the case of the bacteria which are encapsulated in the casein and chitosan microparticles according to formulations Ac, Cc and Dc, the losses after 3 months are about 0.5 logarithmic units, and after 6 months are 3 logarithmic units for formulation Ac, 2 logarithmic units for formulation Dc and of 1 logarithmic unit for formulation Cc.

These results confirm that the formulations described in the present invention allow increasing the bacterial viability under environmental conditions with respect to the lyophilized bacteria in the manner similar to that observed in the case of L. plantarum.

Example 6

Figure 8:
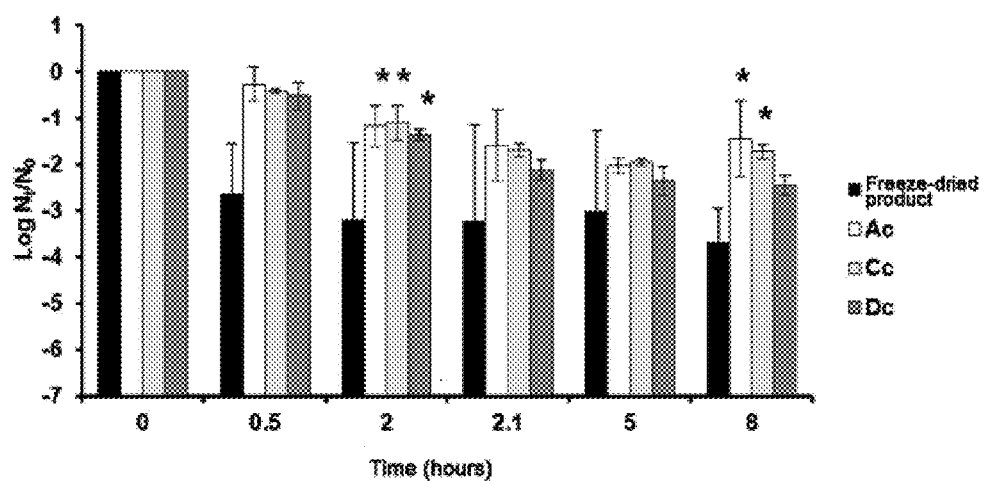
FIG. 8 is a graph showing the survival of *L. casei* in simulated gastrointestinal medium (0 to 2 hours: simulated gastric medium; 2.1 to 8 hours: simulated intestinal medium): non-encapsulated lyophilized *L. casei*; *L. casei* encapsulated in casein microparticles modified with chitosan (formulation Ac); *L. casei* encapsulated in casein microparticles modified with chitosan in the presence of vanillin (formulation Cc); and *L. casei* encapsulated in casein microparticles modified with chitosan in the presence of tripolyphosphate (TPP) (formulation Dc). * Indicates significant differences in the microparticle counts with respect to the freeze-dried product ($p<0.05$).

Evaluation of the Resistance of the Encapsulated Probiotic Bacteria of the Genus *Lactobacillus casei* to Simulated Gastrointestinal Medium Formulations Ac, Cc and Dc described in Example 4 were used to evaluate the resistance of the encapsulated bacteria in a simulated gastrointestinal medium following the method described in Section VII of the "General Methods". FIG. 8 shows the results obtained throughout the study for the microparticles, as well as the resistance obtained for the non-encapsulated lyophilized bacteria.

In the case of the free bacteria (non-encapsulated lyophilized bacteria), the number of viable counts decreased significantly (4 logarithmic units) in the two first hours of study in gastric medium and it was kept constant thereafter. However, the data show that the encapsulated bacteria are significantly more resistant to treatment in gastric medium, reaching the end of the treatment with average losses of about 1.5 logarithmic units. Furthermore, in the case of formulations Ac and Cc, after passage through the intestinal medium, the resistance of the bacteria decreased although it remained significantly greater than the lyophilized control, an effect which was not observed for formulation Dc.

These results demonstrate that the described microparticles increase the tolerance of the studied bacteria to the simulated gastrointestinal conditions.

Example 7

Immunological Study of Casein Biocapsules Associated with *L. plantarum*

To carry out this example, casein microparticles modified with chitosan in the presence of vanillin described in Example 1 (reference Bp) were used. To that end, 0.5 mL of vanillin (5 mg/mL) were added to 25 mL of a 10 mg/mL aqueous solution of sodium caseinate. After (at least) 15 minutes of incubation, 1 mL of the bacterial suspension ($4.6 \times 10^{10}$ CFU/mL) described in Section III of the "General Methods" were added to the mixture, after being centrifuged and resuspended in a solution of 2% sucrose (w/v). 2 mL of a chitosan solution having a concentration of 1.6 mg/mL prepared in an aqueous medium with pH 5.5-6 were then added to the mixture.

100 mg of mannitol were added five minutes later to the preceding mixture and the formulation was then dried using the spray-drying technique. The processing conditions were the following:

Air inlet temperature: 85° C.
Air outlet temperature: 40-45° C.
Air pressure: 6 bar ($6 \times 10^5$ Pa)
Sample pumping rate: 3.5 mL/min
Suction: 100%
Airflow: 600 L/h.

The microparticles obtained in the form of powder were again collected for characterization and quantification. The mean size of the microparticles obtained was 7±4 µm. On the other hand, the bacteria count gave a titer of $5.1 \times 10^{10}$ CFU per gram of microparticles The immunological studies were conducted according to the regulations of the Ethics Committee of the Institution as well as to the European legislation on experimental animals (86/609/EU). To that end, 24 male CD1 mice (Charles River) having a mean weight of 20 g were used, they were subjected to normal light-dark conditions (12 hours-12 hours). The animals were divided into 4 different groups (6 mice per group) and each group received a different daily treatment for 21 successive days.

0.1 mL of PBS (phosphate buffer saline pH 7.4) was orally administered to the first group (control). A second group was treated with a suspension of *Lactobacillus plantarum* in 2% sucrose with a dose of $10^7$ CFU/mouse (Free LPs). The third group was treated with a physical mixture in the form of suspension formed by *L. plantarum* in 2% sucrose ($10^7$ CFU/mouse) mixed with empty casein microparticles modified with chitosan and cross-linked with vanillin (100 µg/mouse) (physical mixture, MF). Finally, the fourth group received the formulation of *L. plantarum* incorporated in casein microparticles modified with chitosan and cross-linked with vanillin ($10^7$ CFU/mouse) (Bp) described previously.

On day 22, a volume of blood of about 250 µL was drawn using serum separating tubes (SARSTEDT Microtube 1.1 mL Z-Gel). The animals were then sacrificed and the spleens were extracted, the spleen cells were desintegrated in RPMI 1640 medium with glycine at 4° C. The erythrocytes were lysed, the splenocytes being counted, the concentration of which was adjusted in complete RPMI medium. *L. plantarum* was added (in a ratio of 10:1 with respect to splenocytes) as a stimulus to 100 µL replicates of cell suspension. After 48 hours of incubation at 37° C., the cell suspensions were centrifuged and the supernatant containing the cytokines were preserved at −80° C. The cytokines were captured by means of the BD cytometric bead array Th1/Th2/Th17 CBA kit (BD, USA) and determined using a flow cytometer (Attune® Acoustic Focusing Cytometer).

Figure 9:
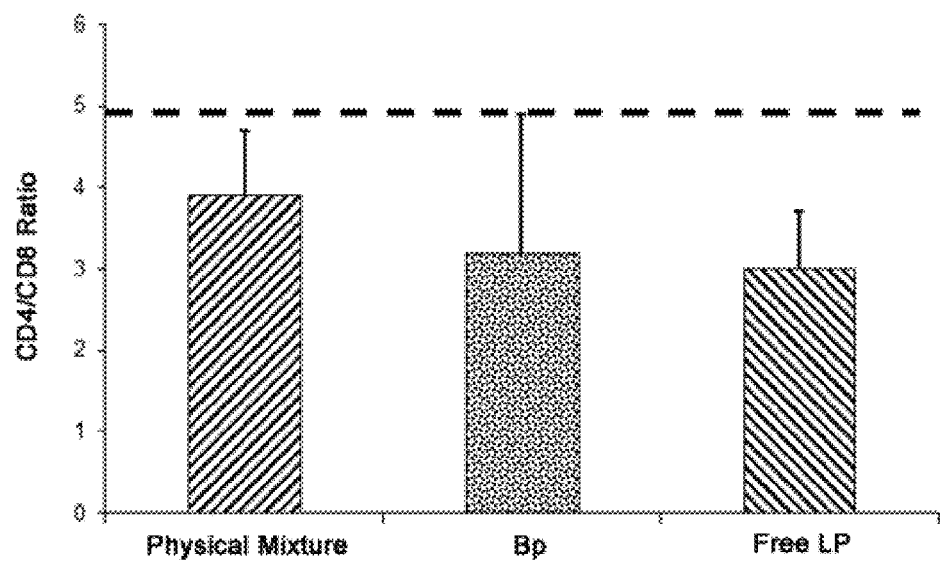
FIG. 9 is a bar chart showing the results of the immunophenotypic analysis of peripheral lymphocytes obtained from mice treated with *L. plantarum* in its non-encapsulated form (free LP), encapsulated *L. plantarum* (Bp) or with the physical mixture of bacteria (*L. plantarum*) and particles (physical mixture). The dotted line shows the ratio obtained in the untreated control group.

FIG. 9 shows how the oral administration of *L. plantarum* (free, encapsulated or with physical mixture) induces a slight increase in the number of cytotoxic lymphocytes which is manifested by a reduction in the $CD4^+/CD8^+$ ratio. This effect is consistent with the data described earlier in the bibliography correlating said increase with an intestine colonizing effect by the bacteria [Herias et al., 1999; Smelt et al., 2012]. On the other hand, it is observed that the encapsulation did not affect the bacteria capacity to alter the $CD4^+/CD8^+$ ratio.

Figure 10:
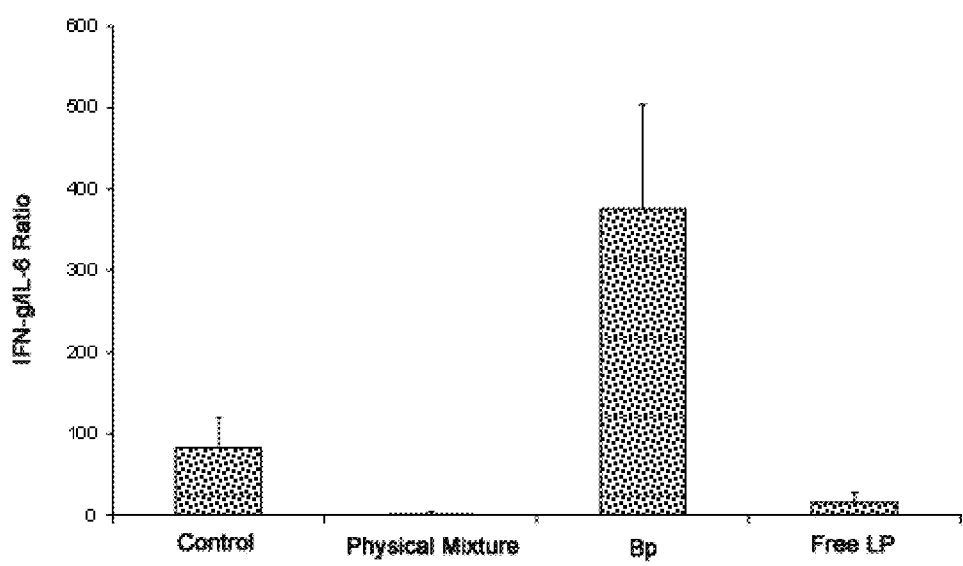
FIG. 10 is a bar chart showing the results of the index of the Th1/Th2 ratio after the in vitro stimulation of peripheral lymphocytes obtained from mice treated with *L. plantarum* in its non-encapsulated form (free LP), encapsulated *L. plantarum* (Bp) or with the physical mixture of bacteria and particles (physical mixture).

FIG. 10 shows the interferon-gamma/interleukin-6 (IL-6) ratio depending on the received treatment. In all the cases, the administration of *L. plantarum* increased interferon-gamma (IFN-g) synthesis. However, the animals treated with the bacterium encapsulated in the microparticles showed a ratio significantly greater than that obtained with the rest of the treatments ($p<0.001$; ANOVA, post hoc Tukey). This shift of the immune response towards a Th1 profile after the administration of *L. plantarum* is consistent with the results obtained by other authors [Smelt et al., 2012; Wiese et al., 2012].

REFERENCES

AYUB, M. A. Z. & BRINQUES, G. B. 2011. Effect of microencapsulation on survival of *Lactobacillus plantarum* in simulated gastrointestinal conditions, refrigeration, and yogurt. *Journal of Food Engineering*, 103, 123-128.

BAO Y, ZHANG Y, ZHANG Y, LIU Y, WANG A Y, DONG X, WANG Y, ZHANG H. 2010. Screening of potential probiotic properties of *Lactobacillus fermentum* isolated from traditional dairy products. *Food Control*, 21 (5): 695-701.

BORGOGNA, M., BELLICH, B., ZORZIN, L., LAPASIN, R. & CESARO, A. 2010. Food microencapsulation of bioactive compounds: Rheological and thermal characterisation of non-conventional gelling system. *Food Chemistry*, 122, 416-423.

BURGAIN, J., GAIANI, C., LINDER, M. & SCHER, J. 2011. Encapsulation of probiotic living cells: From laboratory scale to industrial applications. *Journal of Food Engineering*, 104, 467-483.

DE VOS, P., FAAS, M. M., SPASOJEVIC, M. & SIKKEMA, J. 2010. Encapsulation for preservation of functionality and targeted delivery of bioactive food components. *International Dairy Journal*, 20, 292-302.

DING, W. K. & SHAH, N. P. 2008. Survival of Free and Microencapsulated Probiotic Bacteria in Orange and Apple Juices. *International Food Research Journal*, 15, 219-232.

FERRANDINI, E., CASTILLO, M., LÓPEZ, M. B. & LAENCINA, J. 2006. Modelos estructurales de la micela de caseína. *An. Vet. (Murcia)*, 22, 5-18.

GBASSI, G. K., VANDAMME, T., ENNAHAR, S. & MARCHIONI, E. 2009. Microencapsulation of *Lactobacillus plantarum* spp in an alginate matrix coated with whey proteins. *International Journal of Food Microbiology*, 129, 103-105.

HEIDEBACH, T., FORST, P. & KULOZIK, U. 2009. Transglutaminase-induced caseinate gelation for the microencapsulation of probiotic cells. *International Dairy Journal*, 19, 77-84.

HEIDEBACH, T., FORST, P. & KULOZIK, U. 2010. Influence of casein-based microencapsulation on freeze-drying and storage of probiotic cells. *Journal of Food Engineering*, 98, 309-316.

HEIDEBACH, T., LEEB, E., FOERST, P. & KULOZIK, U. 2011. Microencapsulation of probiotic cells. In: MONZER FANUN, C.-P. (ed.) *Colloids in Biotechnology*.

HERIAS M. V., HESSLE C., TELEMO E., MIDTVEDT T., HANSON L. A., WOLD A. E., Immunomodulatory effects of *Lactobacillus plantarum* colonizing the intestine of gnotobiotic rats. Clin Exp Immunol. 1999 May; 116(2): 283-290.

HIDALGO et al. *Ars Pharm* 2008; 49 (3):245-257.

KARIMI, R., A. M. MORTAZAVIAN AND A. G. DA CRUZ. 2011. Viability of probiotic microorganisms in cheese during production and storage: a review. Dairy Sci Technol 91:283-308

LACROIX, C. & PICOT, A. 2004. Encapsulation of *bifidobacteria* in whey protein-based microcapsules and survival in simulated gastrointestinal conditions and in yoghurt. *International Dairy Journal*, 14, 505-515.

MATTILA-SANDHOLM, T. & SAARELA, M. (eds.) 2003. *Functional Dairy Products*., Boca Raton: Woodhead Publishing Limited Abington Cambridge England CRC. Press LLC.

MOHAMMADI R., A. M. MORTAZAVIAN, R. KHOSROKHAVAR AND A. G. CRUZ. 2011. Probiotic ice cream: viability of probiotic bacteria and sensory properties. Ann Microbiol 61:411 424.

MOHAMMADI, R. AND MORTAZAVIAN A. M. 2011. Review Article: Technological Aspects of Prebiotics in Probiotic Fermented Milks. Food Rev Int 27:192-212.

MORTAZAVIAN, A., RAZAVI, S. H., EHSANI, M. R. & SOHRABVANDI, S. 2007. Principles and methods of microencapsulation of probiotic microorganisms. *IRANIAN JOURNAL of BIOTECHNOLOGY*, 5, 1-18.

OLIVEIRA, A. C., MORETTI, T. S., BOSCHINI, C., BALIERO, J. C., FREITAS, O. & FAVARO-TRINDADE, C. S. 2007. Stability of microencapsulated *B. lactis* (BI 01) and *L. acidophilus* (LAC 4) by complex coacervation followed by spray drying. *Journal of Microencapsulation*, 24, 673-81.

PÉREZ-LUYO, A. 2008. Probióticos: Una alternativa en la prevención de la caries dental?. *Rev Estomatol Herediana*, 18, 65-68.

SANDERS, M. E. 1999. Probiotics. *Food Technology*, 53, 67-77.

SHAH, N. P., DONKOR, O. N., NILMINI, S. L. I., STOLIC, P. & VASILJEVIC, T. 2007. Survival and activity of selected probiotic organisms in set-type yoghurt during cold storage. *International Dairy Journal*, 17, 657-665.

SHAH, N. P. & LANKAPUTHRA, W. E. V. 1997. Improving viability of *Lactobacillus acidophilus* and *Bifidobacterium* spp. in yogurt. *International Dairy Journal*, 7, 349-356.

SMELT M J, DE HAAN B J, BRON P A, VAN SWAM I, MEIJERINK M, et al. (2012) *L. plantarum*, *L. salivarius*, and *L. lactis* Attenuate Th2 Responses and Increase Treg Frequencies in Healthy Mice in a Strain Dependent Manner. PLoS ONE 7(10): e47244. doi:10.1371/journai-.pone.0047244.

VINDEROLA, C. G., W. PROSELLO, T. D. GHIBERTO AND J. A. REINHEIMER (2000a). Viability of probiotic (*Bifidobacterium*, *Lactobacillus acidophilus* and *Lactobacillus casei*) and non probiotic microflora in Argentinian fresco cheese. J Dairy Sci 83:1905-1911.

VINDEROLA, C. G., & REINHEIMER, J. A. (2003). Lactic acid starter and probiotic bacteria: A comparative "in vitro" study of probiotic characteristics and biological barrier resistance. Food Research International, 36, 895-904.

WIESE M., ELJASZEWICZ A., ANDRYSZCZYK M., GRONEK S., GACKOWSKA L., KUBISZEWSKA I., KASZEWSKI W., HELMIN-BASA A., JANUSZEWSKA M., MOTYL I., WIECZYNSKA J., MICCHALKIEWICZ, Immunomodulatory effects of *Lactobacillus plantarum* and *Helicobacter pylori* CagA+ on the expression of selected superficial molecules on monocyte and lymphocyte and the synthesis of cytokines in whole blood culture. J Physiol. Pharmacol., 2012, 63, 3 217-224.

The invention claimed is:

1. A microparticle comprising a matrix and a probiotic bacterium, wherein said matrix consists of casein and chitosan, wherein the chitosan:casein by weight ratio is 1:14 to 1:40, and wherein the microparticle has a mean diameter between 1 μm and 40 μm and the molecular weight of chitosan ranges from 40 kDa to 200 kDa.

2. The microparticle according to claim 1, wherein the probiotic bacterium is a bacterium of the genus *Bifidobacterium* or *Lactobacillus*.

3. A composition comprising a plurality of microparticles as defined in claim 1.

4. The composition according to claim 3, wherein said microparticles are in the form of a dry powder.

5. A microparticle comprising a matrix and a probiotic bacterium, wherein said matrix consists of casein, chitosan and a cross-linking agent, wherein the chitosan:casein by weight ratio is 1:14 to 1:40, and wherein the microparticle has a mean diameter between 1 µm and 40 µm and the molecular weight of chitosan ranges from 40 kDa to 200 kDa.

6. The microparticle according to claim 5, wherein said cross-linking agent is: a divalent metal cation selected from the group consisting of $Ca^{2+}$, $Mg^{2+}$, $Zn^{2+}$, $Fe^{2+}$ and combinations thereof; a tripolyphosphate; vanillin; genipin; or combinations thereof.

7. A composition comprising a plurality of microparticles as defined in claim 5.

8. The composition according to claim 7, selected from the groups consisting of:
   a composition A, comprising:
      casein, between 40% and 60% by weight,
      chitosan, between 0.1% and 3.5% by weight,
      probiotic bacteria, between $10^9$ CFU/g and $5 \times 10^{12}$ CFU/g,
      sodium tripolyphosphate, between 0% and 0.15% by weight, and
      protective agent, between 0% and 60% by weight;
      where the proportions by weight refer to the total weight of the composition;
   a composition B, comprising:
      casein, between 40% and 60% by weight,
      chitosan, between 0.1% and 3.5% by weight,
      probiotic bacteria, between $10^9$ CFU/g and $5 \times 10^{12}$ CFU/g,
      vanillin, between 0% and 0.6% by weight, and
      protective agent, between 0% and 60% by weight;
      where the proportions by weight refer to the total weight of the composition; and
   a composition C, comprising:
      casein, between 40% and 60% by weight,
      chitosan, between 0.1% and 3.5% by weight,
      probiotic bacteria, between $10^9$ CFU/g and $5 \times 10^{12}$ CFU/g,
      $Ca^{2+}$, between 0% and 10% by weight, and
      protective agent, between 0% and 60% by weight,
      where the proportions by weight refer to the total weight of the composition.

9. A food, pharmaceutical, cosmeceutical or nutraceutical product comprising at least one microparticle as defined in claim 1, and a food, pharmaceutical, cosmeceutical, or nutraceutical acceptable vehicle, respectively.

10. An immune system modulating composition comprising a microparticle as defined in claim 1.

11. A method for obtaining the microparticles as defined in claim 1, which comprises mixing casein or a casein source, probiotic bacteria and chitosan to form a suspension containing the formed microparticles.

12. The method according to claim 11, which further comprises drying the suspension containing the formed microparticles.

13. The method according to claim 12, wherein said suspension containing the microparticles is dried in the presence of a protective agent.

14. A method for obtaining the microparticles as defined in claim 5, which comprises mixing casein or a casein source, probiotic bacteria, chitosan and a cross-linking agent.

15. A microparticle obtainable by means of a method according to claim 11.

16. A method for the prevention or treatment of an immune system impairment or pathology in a subject, said method comprising orally administering to a subject in need of such treatment a prophylactic or therapeutic effective amount of a microparticle as defined in claim 1.

17. The method according to claim 16, wherein the immune system impairment or pathology is Th2-mediated transplant rejection, allergies and allergy-associated diseases, immunodeficiencies and pathologies derived from said immunodeficiencies, infections caused by intracellular pathogens, or mucosal infections.

18. The method as defined in claim 17, wherein said allergy is allergies to plant pollens, allergies to animals, food allergies, allergies to metals, or the combinations thereof,
   wherein said allergy-associated disease is asthma or atopic dermatitis,
   wherein said immunodeficiency is a physiological immunodeficiency, a congenital immunodeficiency, or an acquired immunodeficiency, and
   wherein said intracellular pathogen is an eukaryotic pathogen, a prokaryotic pathogen or a virus.

19. The method according to claim 17, wherein the immune system impairment or pathology is a mucosal infection.

20. The method according to claim 19, wherein said mucosa is oral cavity mucosa, gastrointestinal tract mucosa, urogenital tract mucosa or respiratory tract mucosa.

21. The method according to claim 16, wherein the microparticles are in the form of a dry powder in said immune system modulating composition.

* * * * *